United States Patent
Hosokawa et al.

(10) Patent No.: US 8,278,819 B2
(45) Date of Patent: Oct. 2, 2012

(54) ORGANIC ELECTROLUMINESCENCE DEVICE AND DISPLAY

(75) Inventors: Chishio Hosokawa, Sodegaura (JP); Takayasu Sado, Sodegaura (JP); Kiyoshi Ikeda, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 935 days.

(21) Appl. No.: 12/044,436

(22) Filed: Mar. 7, 2008

(65) Prior Publication Data
US 2008/0254319 A1 Oct. 16, 2008

(30) Foreign Application Priority Data

Mar. 9, 2007 (JP) .................. 2007-061091

(51) Int. Cl.
*H01L 51/54* (2006.01)
*C09K 11/06* (2006.01)
(52) U.S. Cl. ........ 313/504; 313/506; 428/690; 428/917; 257/40; 257/E51.041; 257/E51.049
(58) Field of Classification Search .................. None
See application file for complete search history.

(56) References Cited

U.S. PATENT DOCUMENTS
4,539,507 A * 9/1985 VanSlyke et al. ............. 313/504
(Continued)

FOREIGN PATENT DOCUMENTS
JP 03-162481 7/1991
(Continued)

OTHER PUBLICATIONS

C.W. Tang, et al.; "Organic electroluminescent diodes"; Applied Physics Letters; Sep. 21, 1987; vol. 51 (12), pp. 913-915.
(Continued)

*Primary Examiner* — Jennifer Chriss
*Assistant Examiner* — Brett A Crouse
(74) *Attorney, Agent, or Firm* — Oblon, Spivak, McClelland, Maier & Neustadt, L.L.P.

(57) ABSTRACT

In an organic electroluminescence device including a cathode and an anode, at least an emitting layer and an electron transporting layer are provided between the cathode and the anode. The emitting layer contains a host material formed of a naphthacene derivative represented by the following formula (1) and a dopant material formed of a compound having a pyrromethene skeleton represented by the following formula (2) or a metal complex of the compound. The electron transporting layer is preferably a benzoimidazole derivative.

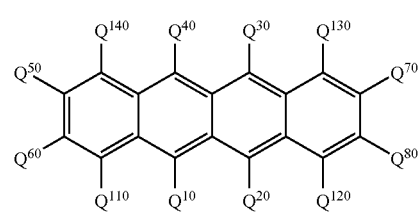

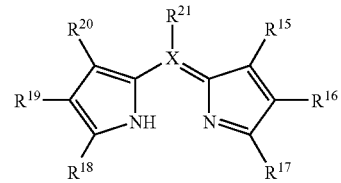

18 Claims, 1 Drawing Sheet

U.S. PATENT DOCUMENTS

| | | | |
|---|---|---|---|
| 2003/0027016 A1* | 2/2003 | Ara et al. | 428/690 |
| 2003/0082406 A1* | 5/2003 | Murase et al. | 428/690 |
| 2005/0221120 A1* | 10/2005 | Owczarczyk et al. | 428/690 |
| 2006/0008672 A1 | 1/2006 | Jarikov | |
| 2006/0147747 A1* | 7/2006 | Yamamoto et al. | 428/690 |
| 2010/0108992 A1* | 5/2010 | Ikeda et al. | 257/40 |
| 2012/0037890 A1* | 2/2012 | Okuda et al. | 257/40 |

FOREIGN PATENT DOCUMENTS

| | | |
|---|---|---|
| JP | 03-200889 | 9/1991 |
| JP | 07-138561 | 5/1995 |
| JP | 08-239655 | 9/1996 |
| JP | 08-311442 | 11/1996 |
| JP | 2001-081451 | 3/2001 |
| JP | 2001-257077 | 9/2001 |
| JP | 2001-307885 | 11/2001 |
| JP | 2002-008867 | 1/2002 |
| JP | 2003-040845 | 2/2003 |
| JP | 2003-081924 | 3/2003 |
| JP | 2003-086379 | 3/2003 |
| JP | 2003-338377 | 11/2003 |
| JP | 2004-200162 | 7/2004 |
| JP | 2004-311030 | 11/2004 |
| JP | 2005-154534 | 6/2005 |
| JP | 2006-245172 | 9/2006 |
| WO | WO 01/23497 | 4/2001 |
| WO | WO 2004/080975 A1 | 9/2004 |
| WO | 2005/075600 | 8/2005 |
| WO | 2007/105448 | 9/2007 |
| WO | 2008/047744 | 4/2008 |

OTHER PUBLICATIONS

U.S. Appl. No. 12/044,291, filed Mar. 7, 2008, Hosokawa, et al.
U.S. Appl. No. 12/098,095, filed Apr. 4, 2008, Sado, et al.
Extended Supplementary European Search Report issued on Mar. 23, 2011 in corresponding European Application No. 08 72 1707.
Notice of Reason(s) for Rejection issued Feb. 28, 2012 in Japanese Patent Application No. 2009-504044 (with English translation).

* cited by examiner

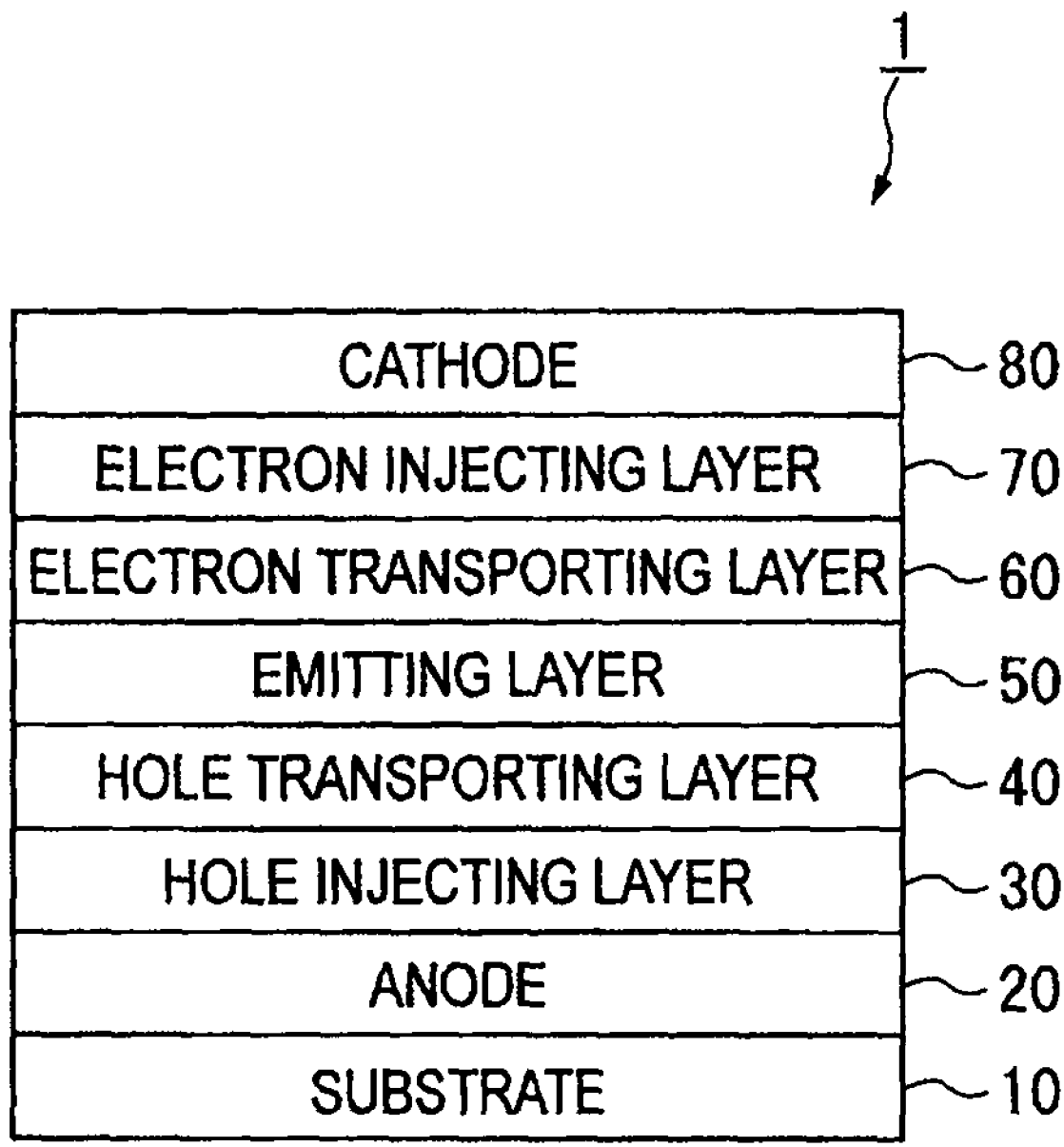

ORGANIC ELECTROLUMINESCENCE DEVICE AND DISPLAY

BACKGROUND OF THE INVENTION

1. Field of the Invention

The present invention relates to an organic electroluminescence device (organic EL device) and a display that use a naphthacene derivative and a compound having a pyrromethene skeleton or a metal complex of the compound together.

2. Description of Related Art

Organic electroluminescence (EL) devices have been known. Organic EL devices formed from organic materials have been vigorously studied since a report on a low voltage-driven organic EL device formed by laminating layers was made by C. W. Tang et al. of Eastman Kodak Company (see Document 1: Applied Physics Letters, vol. 51, page 913, by C. W. Tang and S. A. Vanslyke, 1987).

Known examples of an emitting material used for an organic EL device are a chelate complex such as a tris(8-quinolinol)aluminum (Alq) complex, a coumarin complex, a tetraphenylbutadiene derivative, a bisstyrylarylene derivative, an oxadiazole derivative or the like. These emitting materials, which have been reported to emit blue to red light in a visible region, are expected to be applied to color-display devices (e.g., Document 2: JP-A-08-239655, Document 3: JP-A-07-138561, Document 4: JP-A-03-200889 and the like). However, luminous efficiency and lifetime of such a device has been so insufficient that the device has not been practically applicable. While a full color display requires three primary colors of blue, green and red, among them, a red-emitting device with high efficiency has been demanded.

For instance, Document 5 (JP-A-08-311442) has recently disclosed a red-emitting device whose emitting layer is added with a naphthacene derivative or a pentacene derivative. However, although the red-emitting device is excellent in purity of red color, the red-emitting device requires voltage of 11V to be applied, and time lapsed until the luminescent intensity decreases to half is approximately 150 hours, i.e., the performance of the device is insufficient. Document 6 (JP-A-03-162481) discloses a device whose emitting layer is added with a dicyanomethylene (DCM)-based compound. However, the device exhibits insufficient purity of red color. Document 7 (JP-A-2001-81451) discloses a red-emitting device whose emitting layer is added with an amine-based aromatic compound. However, although the emitting device exhibits excellent CIE (Commission Internationale d'Eclairage) chromaticity (0.64, 0.33) and chromatic purity, the device requires high voltage for driving. Document 8 (WO/01/23497) and Document 9 (JP-A-2003-40845) disclose devices in which an amine-based aromatic compound and an Alq compound are used for the emitting layer. However, although emitting red light, the device exhibits low efficiency and short lifetime.

Document 10 (JP-A-2003-81924) discloses devices in which an amine-based aromatic compound and DPVDPAN are used for the emitting layer. However, high-efficient one of the devices emits orange light while red-emitting one of the devices exhibits low efficiency.

Document 11 (JP-A-2001-307885) discloses a device in which a dicyanoanthracene derivative and an indenoperylene derivative are used for the emitting layer while a metal complex is used for the electron transporting layer. However, the device emits light of red orange color.

Document 12 (JP-A-2003-338377) discloses a device in which a fluoranthene derivative and an indenoperylene derivative are used for the emitting layer while a fluoranthene derivative is used for the electron transporting layer. However, the device does not exhibit practically-applicable efficiency.

SUMMARY OF THE INVENTION

An object of the present invention is to provide an practically-applicable organic EL device and a practically-applicable display excellent in efficiency, lifetime and chromatic purity.

After conducting concentrated studies in order to achieve such an object, the inventors have found that an organic EL device exhibits longer lifetime and higher efficiency by using a naphthacene derivative and a compound having a pyrromethene skeleton or a metal complex of the compound in at least one layer of organic compound layers of the organic EL device, and reached the present invention.

An organic electroluminescence device according to an aspect of the present invention includes: a cathode; an anode; and an emitting layer provided between the cathode and the anode, in which the emitting layer comprises a host and a dopant, the host is a naphthacene derivative represented by a formula (1) as follows, and the dopant is a compound having a pyrromethene skeleton represented by a formula (2) as follows or a metal complex of the compound.

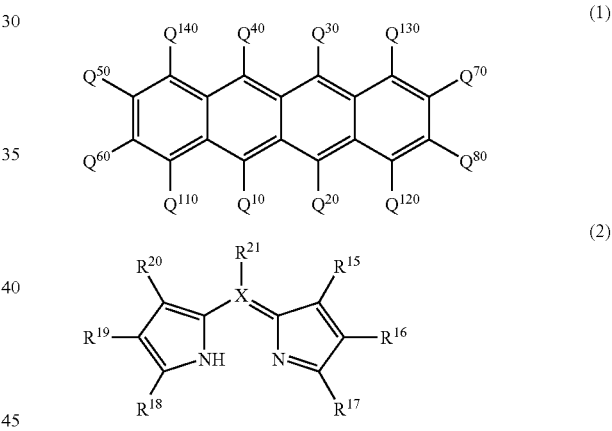

In the formula (1), $Q^{10}$, $Q^{20}$, $Q^{30}$, $Q^{40}$, $Q^{50}$, $Q^{60}$, $Q^{70}$, $Q^{80}$, $Q^{110}$, $Q^{120}$, $Q^{130}$ and $Q^{140}$ each represent a hydrogen atom, a substituted or unsubstituted alkyl group having 1 to 20 carbon atoms, a substituted or unsubstituted aryl group having 6 to 30 carbon atoms, a substituted or unsubstituted amino group, a substituted or unsubstituted alkoxy group having 1 to 20 carbon atoms, a substituted or unsubstituted alkylthio group having 1 to 20 carbon atoms, a substituted or unsubstituted aryloxy group having 6 to 30 carbon atoms, a substituted or unsubstituted arylthio group having 6 to 30 carbon atoms, a substituted or unsubstituted alkenyl group, a substituted or unsubstituted aralkyl group having 7 to 30 carbon atoms or a substituted or unsubstituted heterocyclic group. $Q^{10}$, $Q^{20}$, $Q^{30}$, $Q^{40}$, $Q^{50}$, $Q^{60}$, $Q^{70}$, $Q^{80}$, $Q^{110}$, $Q^{120}$, $Q^{130}$ and $Q^{140}$ may be mutually the same or different.

In the formula (2), at least one of $R^{15}$ to $R^{21}$ is a substitute having an aromatic ring or forms a condensed ring together with an adjacent substituent while the rest of $R^{15}$ to $R^{21}$ each represent a hydrogen atom, an alkyl group, a cycloalkyl group, an aralkyl group, an alkenyl group, a cycloalkenyl group, an alkynyl group, a hydroxyl group, a mercapto group, an alkoxy group, an alkylthio group, an arylether group, an arylthioether group, an aryl group, a heterocyclic group, halogen, a haloalkane, a haloalkene, a haloalkyne, a cyano group, an aldehyde group, a carbonyl group, a carboxyl group, an ester group, a carbamoyl group, an amino group, a nitro group, a silyl group or a siloxanyl group. The rest of $R^{15}$ to $R^{21}$ each may form a condensed ring or an aliphatic ring with an adjacent substituent (the groups listed above each have 1 to 20 carbon atoms). $R^{15}$ to $R^{21}$ may be mutually the same or different and may be substituted or unsubstituted. X represents a carbon atom or a nitrogen atom on a condition that $R^{21}$ above does not exist when X represents a nitrogen atom. A metal in the metal complex is at least one metal selected from a group consisting of boron, beryllium, magnesium, chrome, iron, cobalt, nickel, copper, zinc and platinum.

The metal in the metal complex is particularly preferably boron.

The substituted or unsubstituted alkyl group is preferably an alkyl group having 1 to 20 carbon atoms, more preferably an alkyl group having 1 to 10 carbon atoms, further preferably an alkyl group having 1 to 5 carbon atoms. The alkyl group may be linear or branched. The alkyl group may be a primary alkyl group, a secondary alkyl group or a tertiary alkyl group.

Preferable examples of the alkyl group are a methyl group, an ethyl group, an n-propyl group, an isopropyl group, an n-butyl group, a sec-butyl group, a tert-butyl group, an n-pentyl group, an n-hexyl group, an n-heptyl group, an n-octyl group, an n-nonyl group and an n-decyl group.

The substituted or unsubstituted aryl group is preferably an aryl group having 6 to 30 carbon atoms, more preferably an aryl group having 6 to 20 carbon atoms. Examples of the aryl group are a phenyl group, a phenylphenyl group (4-phenylphenyl group, 3-phenylphenyl group, 2-phenylphenyl group), a naphthylphenyl group (4-(1-naphthyl)phenyl group, 4-(2-naphthyl)phenyl group), a naphthyl group (1-naphthyl group, 2-naphthyl group), a phenylnaphthyl group (6-phenyl-2-naphthyl group, 4-phenyl-1-naphthyl group), a naphthylnaphthyl group (6-naphthyl-2-naphthyl group, 4-naphthyl-1-naphthyl group), an anthranil group, a phenantyl group, a pyrenyl group and a chrysenyl group.

The amino group may be an amino group, a substituted or unsubstituted monoalkyl-aryl group having 1 to 20 carbon atoms, a substituted or unsubstituted dialkyl-aryl group having 1 to 20 carbon atoms, a substituted or unsubstituted monoaryl-aryl group having 6 to 30 carbon atoms, or a substituted or unsubstituted bisaryl-aryl group having 6 to 30 carbon atoms. Examples of the amino group are a dimethylamino group, a diethylamino group, a diphenylamino group, a ditolylamino group and a dixylylamino group.

The substituted or unsubstituted alkoxy group is preferably an alkoxy group having 1 to 20 carbon atoms, examples of which are a methoxy group, an ethoxy group and a propoxy group.

The substituted or unsubstituted alkylthio group is preferably an alkylthio group having 1 to 20 carbon atoms, examples of which are a methylthio group and an ethylthio group.

The substituted or unsubstituted aryloxy group is preferably an aryloxy group having 6 to 30 carbon atoms, an example of which is a phenoxy group.

The substituted or unsubstituted aryloxythio group is preferably an aryloxythio group having 6 to 30 carbon atoms, an example of which is a phenylthio group.

The substituted or unsubstituted alkenyl group is preferably an alkenyl group having 1 to 20 carbon atoms, examples of which are a vinyl group and a propenyl group.

The substituted or unsubstituted aralkyl group is preferably an aralkyl group having 7 to 30 carbon atoms, an example of which is a benzyl group.

The substituted or unsubstituted heterocyclic group is preferably a heterocyclic group having 5 to 30 carbon atoms, examples of which are a pyridyl group, a furyl group, a thienyl group, a pyrazyl group, a pyrimidyl group and a quinolyl group.

According to the aspect of the present invention, since the emitting layer contains the host formed of a naphthacene derivative and the dopant formed of a compound having a pyrromethene skeleton or a metal complex of the compound, the organic EL device having practically-applicable efficiency and lifetime can be realized.

According to the aspect of the present invention, it is preferable that the compound having the pyrromethene skeleton represented by the formula (2) or the metal complex of the compound is a metal complex having a pyrromethene skeleton represented by a formula (2-1) as follows.

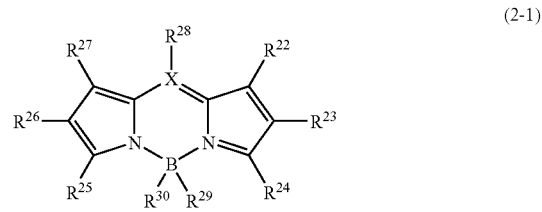

(2-1)

In the formula (2-1), at least one of $R^{22}$ to $R^{28}$ is a substitute having an aromatic ring or forms a condensed aromatic ring together with an adjacent substituent while the rest of $R^{22}$ to $R^{28}$ each represent a hydrogen atom, an alkyl group, a cycloalkyl group, an aralkyl group, an alkenyl group, a cycloalkenyl group, an alkynyl group, a hydroxyl group, a mercapto group, an alkoxy group, an alkylthio group, an arylether group, an arylthioether group, an aryl group, a heterocyclic group, halogen, haloalkane, haloalkene, haloalkyne, a cyano group, an aldehyde group, a carbonyl group, a carboxyl group, an ester group, a carbamoyl group, an amino group, a nitro group, a silyl group or a siloxanyl group. The rest of $R^{22}$ to $R^{28}$ each may form a condensed ring or an aliphatic ring with an adjacent substituent. $R^{22}$ to $R^{28}$ may be mutually the same or different and may be substituted or unsubstituted. $R^{29}$ and $R^{30}$ may be mutually the same or different and each are selected from a group consisting of halogen, a hydrogen atom, substituted or unsubstituted alkyl, substituted or unsubstituted aryl and a substituted or unsubstituted heterocyclic group. X represents a carbon atom or a nitrogen atom on a condition that $R^{28}$ above does not exist when X represents a nitrogen atom.

According to the aspect of the present invention, it is preferable that at least one of $R^{22}$ to $R^{28}$ in the metal complex having the pyrromethene skeleton represented by the formula (2-1) is a substituent having an aromatic ring.

According to the aspect of the present invention, it is preferable that at least one of $R^{22}$ to $R^{28}$ in the metal complex having the pyrromethene skeleton represented by the formula (2-1) forms a condensed aromatic ring together with an adjacent substituent.

According to the aspect of the present invention, it is preferable that at least one of $R^{22}$ to $R^{24}$ in the metal complex having the pyrromethene skeleton represented by the formula (2-1) forms a substituted or unsubstituted condensed aromatic ring together with an adjacent substituent and/or at least one of $R^{25}$ to $R^{27}$ in the metal complex having the pyrromethene skeleton represented by the formula (2-1) forms a substituted or unsubstituted condensed aromatic ring together with an adjacent substituent.

According to the aspect of the present invention, it is preferable that the metal complex having the pyrromethene skeleton represented by the formula (2-1) is a metal complex having a pyrromethene skeleton represented by a formula (2-2) as follows.

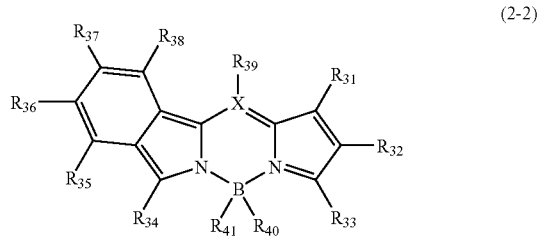

In the formula (2-2), $R_{31}$ to $R_{39}$ each represent a hydrogen atom, an alkyl group, a cycloalkyl group, an aralkyl group, an alkenyl group, a cycloalkenyl group, an alkynyl group, a hydroxyl group, a mercapto group, an alkoxy group, an alkylthio group, an arylether group, an arylthioether group, an aryl group, a heterocyclic group, halogen, haloalkane, haloalkene, haloalkyne, a cyano group, an aldehyde group, a carbonyl group, a carboxyl group, an ester group, a carbamoyl group, an amino group, a nitro group, a silyl group or a siloxanyl group. $R_{31}$ to $R_{39}$ may be mutually the same or different and may be substituted or unsubstituted. $R_{40}$ and $R_{41}$ may be mutually the same or different and each are selected from a group consisting of halogen, a hydrogen atom, substituted or unsubstituted alkyl, substituted or unsubstituted aryl and a substituted or unsubstituted heterocyclic group. X represents a carbon atom or a nitrogen atom on a condition that $R_{39}$ above does not exist when X represents a nitrogen atom.

According to the aspect of the present invention, it is preferable that the metal complex having the pyrromethene skeleton represented by the formula (2-1) is a metal complex having a pyrromethene skeleton represented by a formula (2-3) as follows.

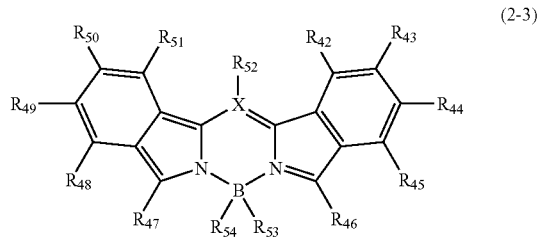

In the formula (2-3), $R_{42}$ to $R_{52}$ each represent a hydrogen atom, an alkyl group, a cycloalkyl group, an aralkyl group, an alkenyl group, a cycloalkenyl group, an alkynyl group, a hydroxyl group, a mercapto group, an alkoxy group, an alkylthio group, an arylether group, an arylthioether group, an aryl group, a heterocyclic group, halogen, haloalkane, haloalkene, haloalkyne, a cyano group, an aldehyde group, a carbonyl group, a carboxyl group, an ester group, a carbamoyl group, an amino group, a nitro group, a silyl group or a siloxanyl group. $R_{42}$ to $R_{52}$ may be mutually the same or different and may be substituted or unsubstituted. $R_{53}$ and $R_{54}$ may be mutually the same or different and each are selected from a group consisting of halogen, a hydrogen atom, a substituted or unsubstituted alkyl, a substituted or unsubstituted aryl and a substituted or unsubstituted heterocyclic group. X represents a carbon atom or a nitrogen atom on a condition that $R_{52}$ above does not exist when X represents a nitrogen atom.

According to the aspect of the present invention, it is preferable that at least one of $Q^{10}$, $Q^{20}$, $Q^{30}$ and $Q^{40}$ in the naphthacene derivative represented by the formula (1) is a substituted or unsubstituted aryl group having 6 to 30 carbon atoms.

According to the aspect of the present invention, it is preferable that the naphthacene derivative represented by the formula (1) is a naphthacene derivative represented by a formula (3) as follows.

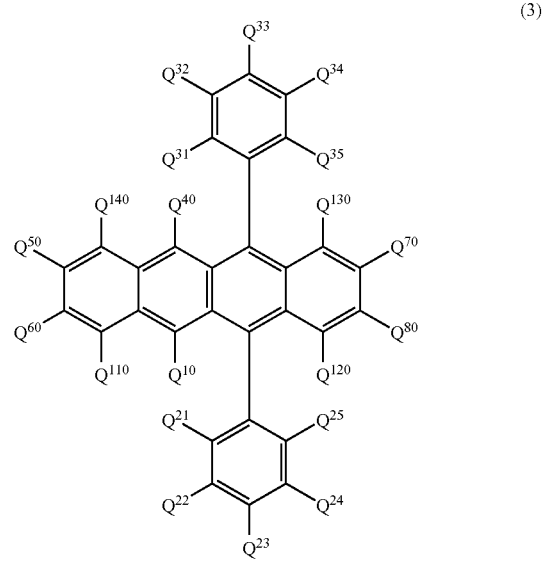

In the formula (3), $Q^{10}$, $Q^{21}$ to $Q^{25}$, $Q^{31}$ to $Q^{35}$, $Q^{40}$ to $Q^{80}$ and $Q^{110}$ to $Q^{140}$ each represent a hydrogen atom, a substituted or unsubstituted alkyl group, a substituted or unsubstituted aryl group, a substituted or unsubstituted amino group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, or a substituted or unsubstituted heterocyclic group. $Q^{10}$, $Q^{21}$ to $Q^{25}$, $Q^{31}$ to $Q^{35}$, $Q^{40}$ to $Q^{80}$ and $Q^{110}$ to $Q^{140}$ may be mutually the same or different.

Adjacent two or more of $Q^{21}$ to $Q^{25}$ and $Q^{31}$ to $Q^{35}$ may be mutually bonded to form a cyclic structure.

According to the aspect of the present invention, it is preferable that at least one of $Q^{21}$, $Q^{25}$, $Q^{31}$ an $Q^{35}$ in the naphthacene derivative represented by the formula (3) represents a substituted or unsubstituted alkyl group, a substituted or unsubstituted aryl group, a substituted or unsubstituted amino group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, or a substituted or unsubstituted heterocyclic group.

According to the above structure, the naphthacene derivative represented by the formula (3) has a substituent in at least one ortho position of two benzene rings bonded to naphthacene.

By introducing substituent(s) to ortho position(s) of the two benzene rings bonded to naphthacene, a steric hindrance is caused between the introduced substituent(s) and the naphthacene skeleton. The steric hindrance directs the introduced substituent(s) to face in an out-of-plane direction of the naphthacene skeleton. Then, the substituent(s) directed in the out-of-plane direction prevents association of naphthacene derivatives with each other.

When two or more of $Q^{21}$, $Q^{25}$, $Q^{31}$ and $Q^{35}$ are substituents, the substituents may be mutually the same or different. In addition, adjacent two or more of $Q^{21}$ to $Q^{25}$ and $Q^{31}$ to $Q^{35}$ may be mutually bonded to form a cyclic structure.

An example of the substituent is a substituted or unsubstituted phenyl group.

Two or more of the ortho positions of the two benzene rings bonded to naphthacene are preferably substituted.

According to the aspect of the present invention, it is preferable that at least one of $Q^{21}$ and $Q^{25}$ in the naphthacene derivative represented by the formula (3) represents a substituted or unsubstituted aryl group or a substituted or unsubstituted heterocyclic group while at least one of $Q^{31}$ and $Q^{35}$ in the naphthacene derivative represents a substituted or unsubstituted aryl group or a substituted or unsubstituted heterocyclic group.

According to the aspect of the present invention, it is preferable that the dopant is contained in the emitting layer at a doping concentration of 0.1 to 10 mass %. It is more preferable that the dopant is contained in the emitting layer at a doping concentration of 0.5 to 2.0 mass %.

According to the aspect of the present invention, it is preferable that the organic EL device further includes an electron transporting layer provided between the cathode and the anode, in which the electron transporting layer comprises a compound represented by a formula (4) as follows.

$$(A)_m\text{-}(B)_n \tag{4}$$

In the formula, A represents a substituted or unsubstituted condensed aromatic hydrocarbon group having three or more rings, and B represents a substituted or unsubstituted heterocyclic group. In addition, m and n each represent an integer in a range of 1 to 6.

According to the aspect of the present invention, it is preferable that A in the compound represented by the formula (4) has a skeleton in its molecule, the skeleton selected from a group consisting of anthracene, phenanthrene, naphthacene, pyrene, chrysene, benzoanthracene, pentacene, dibenzoanthracene, benzopyrene, fluorene, benzofluorene, fluoranthene, benzofluoranthene, naphthofluoranthene, dibenzofluorene, dibenzopyrene and dibenzofluoranthene.

According to the aspect of the present invention, it is preferable that B in the compound represented by the formula (4) is a nitrogen-containing heterocyclic group.

According to the aspect of the present invention, it is preferable that B in the compound represented by the formula (4) has a skeleton in its molecule, the skeleton selected from a group consisting of pyridine, pyrimidine, pyrazine, pyridazine, triazine, quinoline, quinoxaline, acridine, imidazopyridine, imidazopyrimidine, phenanthroline, pyrazole, imidazole and benzoimidazole.

According to the aspect of the present invention, it is preferable that the compound represented by the formula (4) is a benzoimidazole derivative represented by a formula (5) or a formula (6) as follows.

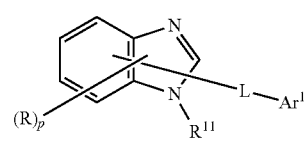

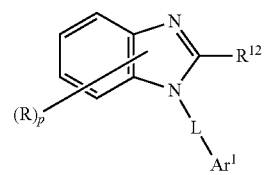

In the formulae: R represents a hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms or a substituted or unsubstituted alkoxy group having 1 to 20 carbon atoms; p represents an integer in a range of 1 to 4; $R^{11}$ represents a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms or an alkoxy group having 1 to 20 carbon atoms; $R^{12}$ represents a hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms or a substituted or unsubstituted alkoxy group having 1 to 20 carbon atoms; L represents a substituted or unsubstituted arylene group having 6 to 60 carbon atoms, a substituted or unsubstituted pyridinylene group, a substituted or unsubstituted quinolinylene group or a substituted or unsubstituted fluorenylene group; and $Ar^1$ represents a substituted or unsubstituted aryl group having 6 to 60 carbon atoms, a substituted or unsubstituted pyridyl group or a substituted or unsubstituted quinolyl group.

At least one of R, $R^{11}$, $R^{12}$, L and $Ar^1$ corresponds to A in the compound represented by the formula (4) and is a condensed aromatic hydrocarbon group having three or more rings.

According to the aspect of the present invention, it is preferable that the emitting layer emits light of orange to red.

A display according to another aspect of the present invention includes the above-described organic electroluminescence device.

According to the above arrangement, since the display is formed from the above-described organic electroluminescence device, the display can exhibit high efficiency, long lifetime and excellent chromatic purity.

The present invention can provide a practically-applicable organic EL device that exhibits high efficiency, long life and excellent chromatic purity.

In addition, according to the present invention, by selecting a suitable compound for the materials of the electron transporting layer and the emitting layer, the organic EL device can exhibit higher efficiency. Specifically, with the arrangement according to the present invention, generation of exciters in the electron transporting layer can be prevented, thereby providing a highly chromatically-pure organic EL device whose micro emission from the electron transporting layer is further reduced In addition, for the same reason(s), the lifetime of the device can be prolonged.

BRIEF DESCRIPTION OF THE DRAWINGS

FIG. 1 shows a first embodiment of an organic EL device according to the present invention.

DETAILED DESCRIPTION OF PREFERRED EMBODIMENT(S)

[Arrangement of Organic EL Device]

Representative exemplary arrangements of an organic EL device usable in the present invention will be described below. As a matter of course, the present invention is not limited thereto.
(1) anode/emitting layer/electron transporting layer/cathode
(2) anode/hole transporting layer/emitting layer/electron transporting layer/cathode
(3) anode/hole injecting layer/hole transporting layer/emitting layer/electron transporting layer/cathode
(4) anode/hole transporting layer/emitting layer/electron transporting layer/electron injecting layer/cathode
(5) anode/hole injecting layer/hole transporting layer/emitting layer/electron transporting layer/electron injecting layer/cathode (FIG. 1)
(6) anode/insulating layer/hole transporting layer/emitting layer/electron transporting layer/cathode
(7) anode/hole transporting layer/emitting layer/electron transporting layer/insulating layer/cathode
(8) anode/insulating layer/hole transporting layer/emitting layer/electron transporting layer/insulating layer/cathode
(9) anode/hole injecting layer/hole transporting layer/emitting layer/electron transporting layer/insulating layer/cathode
(10) anode/insulating layer/hole injecting layer/hole transporting layer/emitting layer/electron transporting layer/electron injecting layer/cathode
(11) anode/insulating layer/hole injecting layer/hole transporting layer/emitting layer/electron transporting layer/electron injecting layer/insulating layer/cathode Among the above, the arrangement (2), (3), (4), (5), (8), (9) or (11) is typically preferable.

The organic EL device according to the present invention includes an anode, a cathode and a single-layered or plural-layered organic layer including an emitting layer. At least one layer of the organic layer contains a host formed of a naphthacene derivative and a dopant formed of a compound having a pyrromethene skeleton or a metal complex of the compound.

An exemplary arrangement of the organic EL device according to the present invention is shown in FIG. 1. In FIG. 1, the organic EL device 1 includes an anode 20, a hole injecting layer 30, a hole transporting layer 40, an emitting layer 50, an electron transporting layer 60, an electron injecting layer 70 and a cathode 80, which are all laminated on a substrate 10 in this order. The hole injecting layer 30, the hole transporting layer 40, the emitting layer 50, the electron transporting layer 60 and the electron injecting layer 70 correspond to the organic layer interposed between the cathode 80 and the anode 20. At least one of the above layers contains a host material formed of a naphthacene derivative and a dopant material formed of a compound having a pyrromethene skeleton or a metal complex of the compound. Preferably, the emitting layer contains a naphthacene derivative and a compound having a pyrromethene skeleton or a metal complex of the compound.

Functions or the like of the layers of the organic EL device will be described below.

[Light-Transmissive Substrate]

When the organic EL device is to emit light through the substrate (i.e., when the organic EL device is bottom-emission type), the organic EL device according to the present invention is manufactured on a light-transmissive substrate. The light-transmissive plate, which supports the organic EL device, is preferably a smoothly-shaped substrate that transmits 50% or more of light in a visible region of 400 nm to 700 nm.

The light-transmissive plate is exemplarily a glass plate, a polymer plate or the like. For the glass plate, such materials as soda-lime glass, barium/strontium-containing glass, lead glass, aluminosilicate glass, borosilicate glass, barium borosilicate glass, quartz and the like can be used. For the polymer plate, such materials as polycarbonate, acryl, polyethylene terephthalate, polyether sulfide, polysulfone and the like can be used. In addition, the light-transmissive plate may be a TFT substrate on which a TFT (thin film transistor) for driving is formed.

On the other hand, when the organic EL device is to emit light from its top portion (i.e., when the organic EL device is top-emission type), the light-transmissive plate is required to be provided with a light reflector, an exemplary material of which is a metal such as aluminum.

[Anode]

The anode of the organic EL device is used for injecting holes into the hole transporting layer or the emitting layer. It is effective that the anode includes a work function of 4.5 eV or more. Exemplary materials for the anode are indium-tin oxide (ITO), tin oxide (NESA), indium zinc oxide alloy (IZO), gold, silver, platinum and copper.

One of the above materials may be singularly used, or alloys formed by mixing the above materials and materials formed by adding other element(s) to the above material(s) may be suitably selected as the material of the anode.

The anode may be made by forming a thin film from the above electrode materials through methods such as vapor deposition and sputtering.

When the organic EL device is bottom-emission type, the anode preferably transmits more than 10% of light emitted by the emitting layer. Sheet resistance of the anode is preferably several hundreds Ω/square or lower. Although depending on the material of the anode, thickness of the anode is typically in a range of 10 nm to 1 μm, and preferably in a range of 10 to 200 nm.

[Emitting Layer]

The emitting layer of the organic EL device has functions described below. Specifically, the emitting layer has:
(i) injecting function: a function for accepting, when an electrical field is applied, the holes injected by the anode or the hole injecting/transporting layer, or the electrons injected by the cathode or the electron injecting/transporting layer;
(ii) transporting function: a function for transporting injected electric charges (the electrons and the holes) by the force of the electrical field; and
(iii) emitting function: a function for providing a condition for recombination of the electrons and the holes to emit light.

Although injectability of the holes may differ from that of the electrons and transporting capabilities represented by mobilities of the holes and the electrons may differ from each other, the emitting layer preferably transports at least either one of the electric charges.

As a method to form the emitting layer, known methods such as vapor deposition, spin coating and an LB (Langmuir Blodgett) method may be employed. The emitting layer is preferably a molecular deposit film.

The molecular deposit film means a thin film formed by depositing a material compound in gas phase or a film formed by solidifying a material compound in a solution state or in liquid phase. The molecular deposit film is generally distinguished from a thin film formed by the LB method (molecular accumulation film) by differences in aggregation structures, higher order structures and functional differences arising therefrom.

As disclosed in JP-A-57-51781, the emitting layer can be formed from a thin film formed by spin coating or the like, the thin film being formed from a solution prepared by dissolving a binder (e.g. a resin) and a material compound in a solvent.

The emitting layer of the present invention contains a host and a dopant.

The emitting layer is preferably doped with a dopant material at a doping concentration of 0.1 to 10 mass %, more preferably 0.5 to 2.0 mass %.

The emitting layer preferably emits light of orange to red.

The host is a naphthacene derivative represented by the above formula (1).

In the formula (1), $Q^{10}$, $Q^{20}$, $Q^{30}$, $Q^{40}$, $Q^{50}$, $Q^{60}$, $Q^{70}$, $Q^{80}$, $Q^{110}$, $Q^{120}$, $Q^{130}$ and $Q^{140}$ each represent a hydrogen atom, a substituted or unsubstituted alkyl group having 1 to 20 carbon atoms, a substituted or unsubstituted aryl group having 6 to 30 carbon atoms, a substituted or unsubstituted amino group, a substituted or unsubstituted alkoxy group having 1 to 20 carbon atoms, a substituted or unsubstituted alkylthio group having 1 to 20 carbon atoms, a substituted or unsubstituted aryloxy group having 6 to 30 carbon atoms, a substituted or unsubstituted arylthio group having 6 to 30 carbon atoms, a substituted or unsubstituted alkenyl group, a substituted or unsubstituted aralkyl group having 7 to 30 carbon atoms or a substituted or unsubstituted heterocyclic group. $Q^{10}$, $Q^{20}$, $Q^{30}$, $Q^{40}$, $Q^{50}$, $Q^{60}$, $Q^{70}$, $Q^{80}$, $Q^{110}$, $Q^{120}$, $Q^{130}$ and $Q^{140}$ may be mutually the same or different.

In the above formula (1), $Q^{10}$, $Q^{20}$, $Q^{30}$ and $Q^{40}$ (collectively referred to as $Q^{10}$ to $Q^{40}$) are each preferably selected from a group consisting of a hydrogen atom, a substituted or unsubstituted alkyl group having 1 to 20 carbon atoms, a substituted or unsubstituted aryl group having 6 to 30 carbon atoms, a substituted or unsubstituted amino group, a substituted or unsubstituted heterocyclic group and a substituted or unsubstituted alkenyl group having 1 to 20 carbon atoms. More preferably, $Q^{10}$ to $Q^{40}$ are aryl groups. Particularly, a structure where $Q^{10}$ and $Q^{40}$ are hydrogen atoms while $Q^{20}$ and $Q^{30}$ are the above substituents is also preferable.

In addition, although a structure where $Q^{10}$ and $Q^{40}$ are the same while $Q^{20}$ and $Q^{30}$ are the same is preferable, $Q^{10}$ to $Q^{40}$ may be mutually different.

In the above formula, $Q^{50}$, $Q^{60}$, $Q^{70}$ and $Q^{80}$ (collectively referred to as $Q^{50}$ to $Q^{80}$) are each preferably selected from a group consisting of a hydrogen atom, a substituted or unsubstituted alkyl group having 1 to 20 carbon atoms, a substituted or unsubstituted aryl group having 6 to 30 carbon atoms, a substituted or unsubstituted amino group, a substituted or unsubstituted alkenyl group having 1 to 20 carbon atoms and a substituted or unsubstituted heterocyclic group. More preferably, $Q^{50}$ to $Q^{80}$ are each a hydrogen atom or a substituted or unsubstituted aryl group having 6 to 30 carbon atoms. In addition, although a structure where $Q^{50}$ and $Q^{60}$ are the same while $Q^{70}$ and $Q^{80}$ are the same is preferable, $Q^{50}$ to $Q^{80}$ may be mutually different. $Q^{110}$, $Q^{120}$, $Q^{130}$ and $Q^{140}$ (collectively referred to as $Q^{110}$ to $Q^{140}$) are each preferably a hydrogen atom.

The alkyl group(s) represented by $Q^{10}$ to $Q^{40}$, $Q^{50}$ to $Q^{80}$ and $Q^{110}$ to $Q^{140}$ may be substituted or unsubstituted, or may be linear or branched. Preferable examples of the alkyl group are a methyl group, an ethyl group, a (n, i)-propyl group, a (n, i, sec, tert)-butyl group, and (n, i, neo, tert)-pentyl group.

The aryl group(s) represented by $Q^{10}$ to $Q^{40}$, $Q^{50}$ to $Q^{80}$ and $Q^{110}$ to $Q^{140}$ may monocyclic or polycyclic, or may be of a condensed-ring structure or of a ring-assembly structure. The aryl group(s) represented by $Q^{10}$ to $Q^{40}$, $Q^{50}$ to $Q^{80}$ and $Q^{110}$ to $Q^{140}$ may be substituted or unsubstituted. The aryl group(s) represented by $Q^{10}$ to $Q^{40}$, $Q^{50}$ to $Q^{80}$ and $Q^{110}$ to $Q^{140}$ is preferably a phenyl group, an (o-, m-, p-) tolyl group, a pyrenyl group, a perylenyl group, a coronenyl group, a (1-, and 2-) naphthyl group, an anthryl group, a (o-, m-, p-) biphenyl group, a taphenyl group and a phenanthryl group.

Although the amino group(s) represented by $Q^{10}$ to $Q^{40}$, $Q^{50}$ to $Q^{80}$ and $Q^{110}$ to $Q^{140}$ may be substituted or unsubstituted, the amino group(s) is preferably substituted and may be an alkylamino group, an arylamino group, an aralkylamino group or the like. The above amino groups each preferably contain fatty series having 1 to 6 carbon atoms in total and/or an aromatic carbon ring having 1 to 4 rings. Examples of such an amino group are a dimethylamino group, a diethylamino group, an abutyl-amino group, a diphenylamino group, a ditolylamino group, a bis-diphenylamino group and a bis-naphtylamino group.

The heterocyclic group(s) represented by $Q^{10}$ to $Q^{40}$, $Q^{50}$ to $Q^{80}$ and $Q^{110}$ to $Q^{140}$ may be substituted or unsubstituted. Examples of the heterocyclic group(s) are a five- or six-membered aromatic heterocyclic group containing O, N and S as heteroatoms and a condensed polycyclic aromatic group having 2 to 20 carbon atoms. Examples of the aromatic heterocyclic group and the condensed polycyclic aromatic heterocyclic group are a thienyl group, a furyl group, a pyronyl group, a pyridyl group, a quinolyl group and a quinoxalyl group.

Preferable Examples of the substituted or unsubstituted alkenyl group(s) having 1 to 20 carbon atoms represented by $Q^{10}$ to $Q^{40}$, $Q^{50}$ to $Q^{80}$ and $Q^{110}$ to $Q^{140}$ are a (1- and 2-) phenylalkenyl group, a (1,2- and 2,2-) diphenylalkenyl group and a (1,2,2-)triphenylalkenyl group that are each substituted by at least one phenyl group. Each of the above examples may be unsubstituted.

The alkoxy group(s) or the alkylthio group(s) represented by $Q^{10}$ to $Q^{40}$, $Q^{50}$ to $Q^{80}$ and $Q^{110}$ to $Q^{140}$ may be substituted or unsubstituted. The alkoxy group(s) or the alkylthio group(s) preferably contains the above-described alkyl group.

The aryloxy group(s) or the arylthio group(s) represented by $Q^{10}$ to $Q^{40}$, $Q^{50}$ to $Q^{80}$ and $Q^{110}$ to $Q^{140}$ may be substituted or unsubstituted. The aryloxy group(s) or the arylthio group(s) preferably has an aryl group. An example of the aryloxy group(s) is an (o-, m-, p-) phenoxy group while an example of the arylthio group(s) is an (o-, m-, p-) phenylthio group.

The aralkyl group(s) represented by $Q^{10}$ to $Q^{40}$, $Q^{50}$ to $Q^{80}$ and $Q^{110}$ to $Q^{140}$ may be substituted or unsubstituted, examples of which are a benzyl group and a phenethyl group.

When $Q^{10}$ to $Q^{40}$, $Q^{50}$ to $Q^{80}$, and $Q^{110}$ to $Q^{140}$ are substituted, at least two of the substituents contained, particularly, in $Q^{10}$ to $Q^{40}$ are each preferably an aryl group, an amino group, a heterocyclic group, an alkenyl group or an aryloxy group, more preferably an aryl group. The same as described in relation to $Q^{10}$ to $Q^{40}$ applies to the aryl group, the amino group, the heterocyclic group and the alkenyl group.

Two or more of the above substituents may form a condensed ring. The above substituents may be further substituted, preferable substituents for which are the same as in the above description.

When $Q^{10}$ to $Q^{40}$, $Q^{50}$ to $Q^{80}$, and $Q^{110}$ to $Q^{140}$ are substituted, at least two, particularly, of $Q^{10}$ to $Q^{40}$ each preferably contain the above substituent. The substitution positions are not subject to any specific limitations. When $Q^{10}$ to $Q^{40}$ contains phenyl, the substitution positions may be any one of meta, para and ortho positions.

In the above formula (1), at least one of $Q^{10}$ to $Q^{80}$ is preferably a substituted or unsubstituted aryl group. More preferably, at least one of $Q^{10}$ to $Q^{40}$ is a substituted or unsubstituted aryl group.

Specifically, the naphthacene derivative is more preferably represented by the above formula (3).

In the formula (3), $Q^{10}$, $Q^{21}$ to $Q^{25}$, $Q^{31}$ to $Q^{35}$, $Q^{40}$ to $Q^{80}$ and $Q^{110}$ to $Q^{140}$ each represent a hydrogen atom, a substituted or unsubstituted alkyl group, a substituted or unsubstituted aryl group, a substituted or unsubstituted amino group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, or a substituted or unsubstituted heterocyclic group. $Q^{10}$, $Q^{21}$ to $Q^{25}$, $Q^{31}$ to $Q^{35}$, $Q^{40}$ to $Q^{80}$ and $Q^{110}$ to $Q^{140}$ may be mutually the same or different. Adjacent two or more of $Q^{21}$ to $Q^{25}$ and $Q^{31}$ to $Q^{35}$ may be mutually bonded to form a cyclic structure.

The same as described in relation to $Q^{10}$ and the like of the formula (1) applies to examples of these groups.

In the formula (3), $Q^{21}$ to $Q^{25}$ and $Q^{31}$ to $Q^{35}$ are each preferably selected from a group consisting of a hydrogen group, an aryl group, an amino group, a heterocyclic group, an aryloxy group and an alkenyl group, more preferably an aryl group. In addition, at least one of $Q^{21}$ to $Q^{25}$ and $Q^{31}$ to $Q^{35}$ is preferably substituted by an aryl group, an amino group, a heterocyclic group or an aryloxy group, more preferably by an aryl group. Adjacent two or more of the above may form a condensed ring. The same as described in relation to $Q^{10}$ to $Q^{40}$ applies to preferable examples of the aryl group, the amino group, the heterocyclic group and the alkenyl group.

In addition, although a structure where $Q^{21}$ to $Q^{25}$ and $Q^{31}$ to $Q^{35}$ are the same is preferable, $Q^{21}$ to $Q^{25}$ may be different from $Q^{31}$ to $Q^{35}$. Examples of the amino group for substituting $Q^{21}$ to $Q^{25}$ and $Q^{31}$ to $Q^{35}$ are an alkylamino group, an arylamino group and an aralkylamino group. The above amino groups each preferably contain fatty series having 1 to 6 carbon atoms in total and/or an aromatic carbon ring having 1 to 4 rings. Examples of such an amino group are a dimethylamino group, a diethylamino group, an abutyl-amino group, a diphenylamino group, a ditolylamino group, a bis-diphenylamino group and a bis-naphtylamino group.

Examples of the condensed ring formed as above are indene, naphthalene, anthracene, phenanthrene, quinoline, isoquinoline, quinoxaline, phenazine, acridine, indole, carbazole, phenoxazine, phenothiazine, benzothiazole, benzothiophen, benzofuran, acridone, benzoimidazole, coumarin and flavone.

$Q^{10}$, $Q^{40}$ and $Q^{110}$ to $Q^{140}$ are each particularly preferably a hydrogen atom.

Examples of the aromatic compound represented by the general formula (1) according to the present invention will be shown below. However, the present invention is not limited to the exemplary compounds shown below.

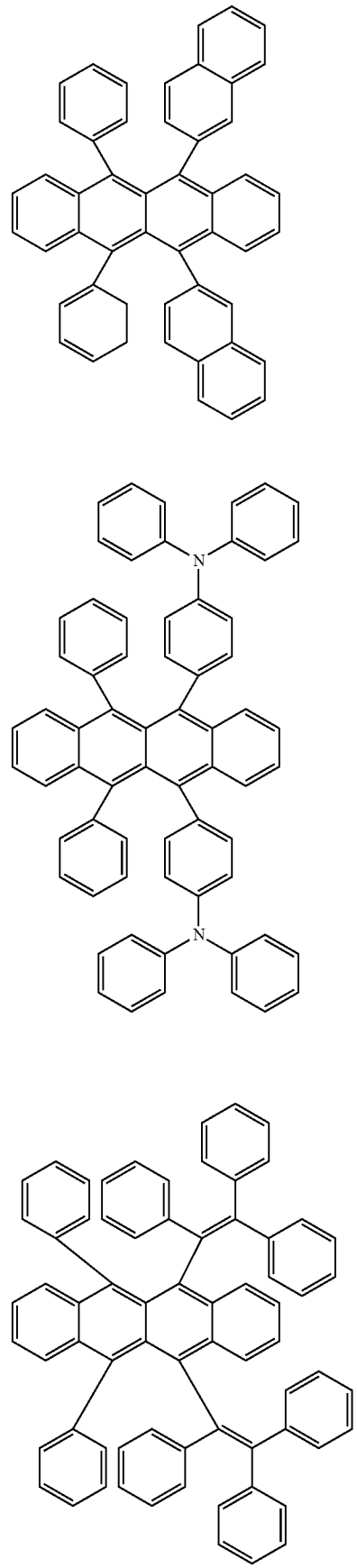

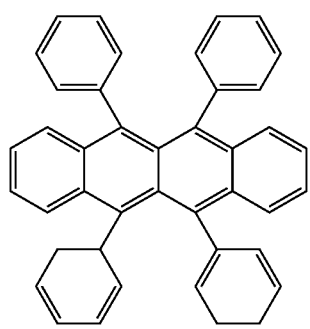
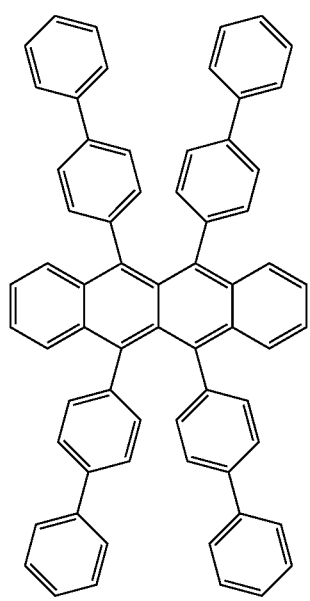
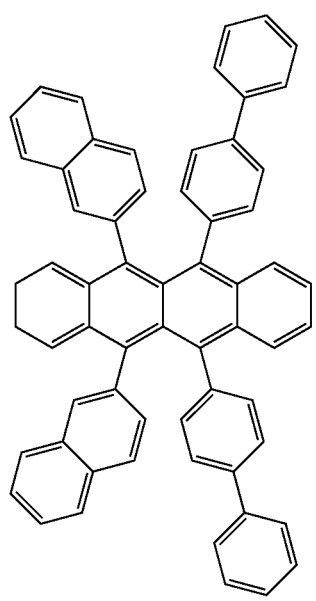
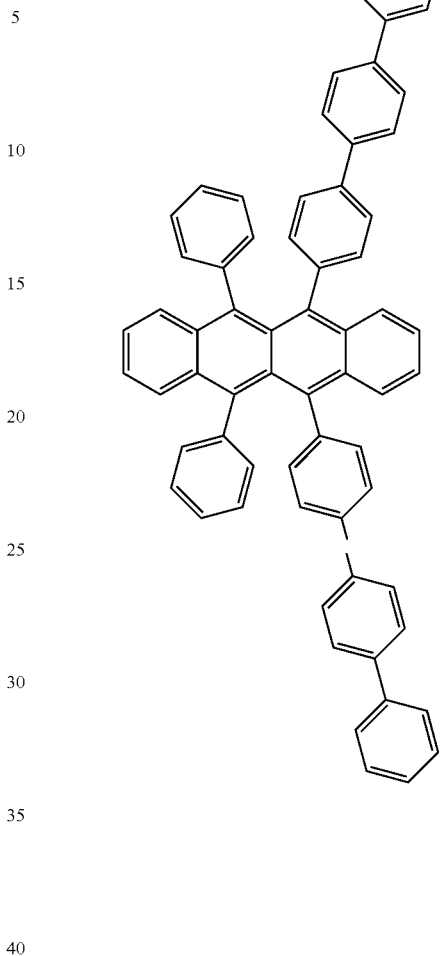
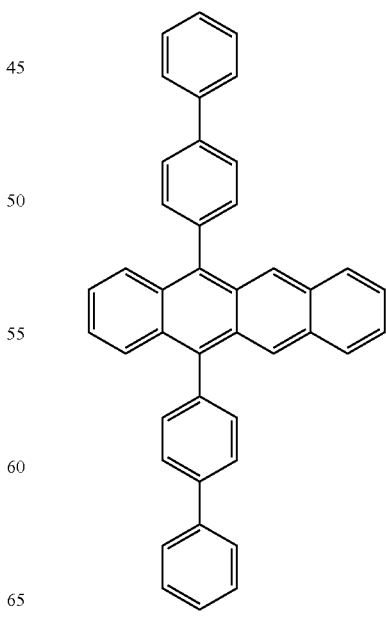

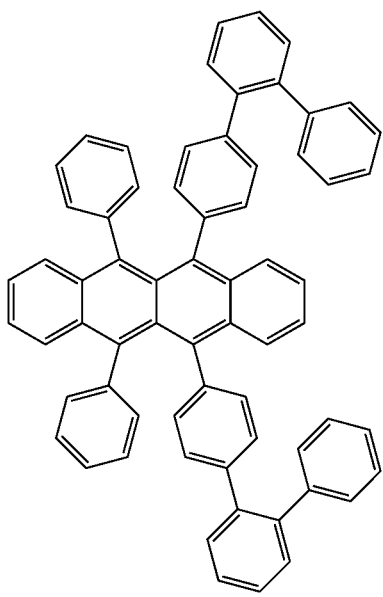
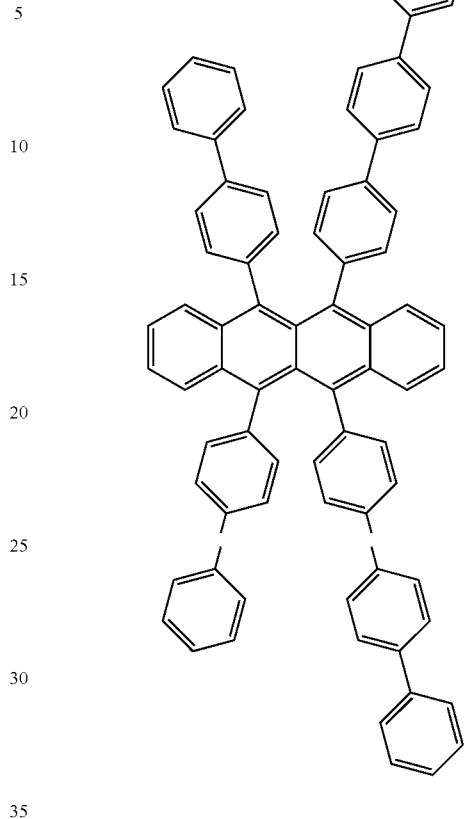
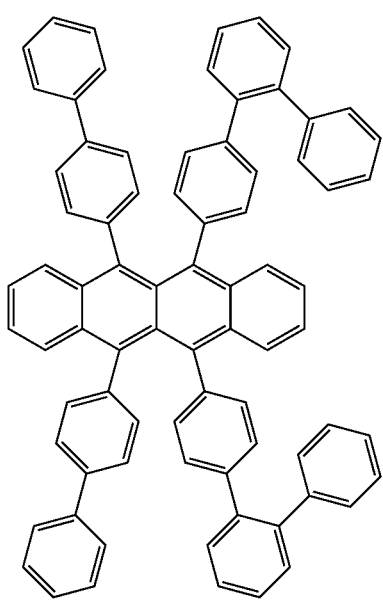
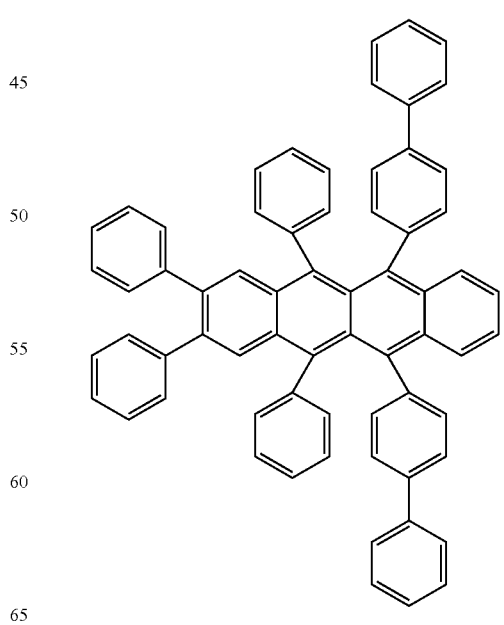

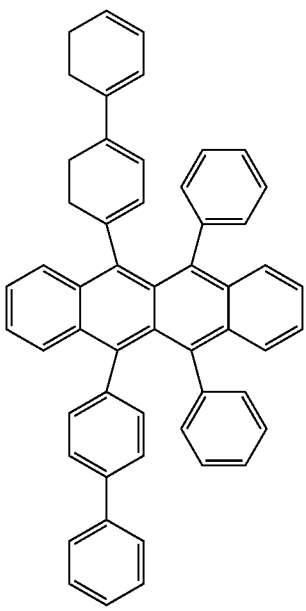

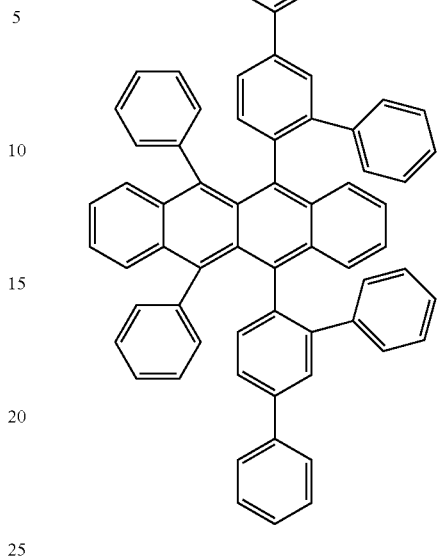

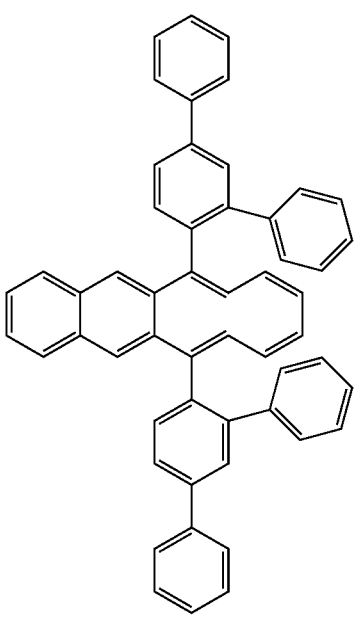

The dopant is a compound having the pyrromethene skeleton represented by the formula (2) or a metal complex of the compound.

The compound having the pyrromethene skeleton represented by the formula (2) or the metal complex of the compound is preferably a compound having a pyrromethene skeleton represented by the following formula (2-1) or a metal complex of the compound.

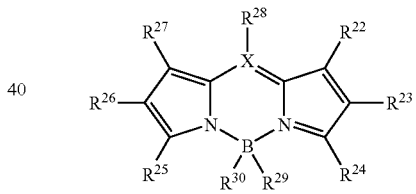

(2-1)

In the formula (2-1), at least one of $R^{22}$ to $R^{28}$ is a substitute having an aromatic ring or forms a condensed aromatic ring together with an adjacent substituent while the rest of $R^{22}$ to $R^{28}$ each represent a hydrogen atom, an alkyl group, a cycloalkyl group, an aralkyl group, an alkenyl group, a cycloalkenyl group, an alkynyl group, a hydroxyl group, a mercapto group, an alkoxy group, an alkylthio group, an arylether group, an arylthioether group, an aryl group, a heterocyclic group, halogen, haloalkane, haloalkene, haloalkyne, a cyano group, an aldehyde group, a carbonyl group, a carboxyl group, an ester group, a carbamoyl group, an amino group, a nitro group, a silyl group or a siloxanyl group. The rest of $R^{22}$ to $R^{28}$ each may form a condensed ring or an aliphatic ring with an adjacent substituent. $R^{22}$ to $R^{28}$ may be mutually the same or different and may be substituted or unsubstituted. $R^{29}$ and $R^{30}$ may be mutually the same or different and each are selected from a group consisting of halogen, a hydrogen atom, substituted or unsubstituted alkyl, substituted or unsubstituted aryl and a substituted or unsubstituted heterocyclic group. X represents a carbon atom or a nitrogen atom on a condition that $R^{28}$ above does not exist when X represents a nitrogen atom.

When one or more of $R^{22}$ to $R^{28}$ forms a condensed aromatic ring(s) together with adjacent substituent(s), the condensed aromatic ring(s) is preferably formed by a pair of $R^{22}$ and $R^{23}$, a pair of $R^{23}$ and $R^{24}$, a pair of $R^{25}$ and $R^{26}$ and/or a pair of $R^{26}$ and $R^{27}$. The condensed aromatic ring(s) is particularly preferably formed by the pair of $R^{22}$ and $R^{23}$ and/or the pair of $R^{26}$ and $R^{27}$. Examples of the condensed aromatic ring(s) are a benzo ring and a naphtho ring.

The compound having the pyrromethene skeleton represented by the formula (2) or the metal complex of the compound is preferably a compound having a pyrromethene skeleton represented by the following formula (2-2) or a metal complex of the compound.

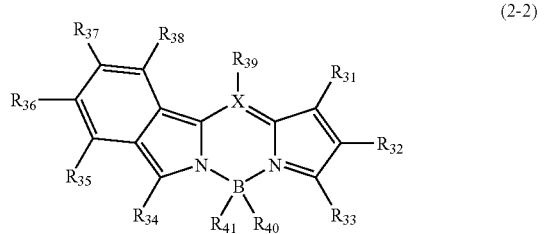

(2-2)

In the formula (2-2), $R_{31}$ to $R_{39}$ each represent a hydrogen atom, an alkyl group, a cycloalkyl group, an aralkyl group, an alkenyl group, a cycloalkenyl group, an alkynyl group, a hydroxyl group, a mercapto group, an alkoxy group, an alkylthio group, an arylether group, an arylthioether group, an aryl group, a heterocyclic group, halogen, haloalkane, haloalkene, haloalkyne, a cyano group, an aldehyde group, a carbonyl group, a carboxyl group, an ester group, a carbamoyl group, an amino group, a nitro group, a silyl group or a siloxanyl group. $R_{31}$ to $R_{39}$ may be mutually the same or different and may be substituted or unsubstituted. $R_{40}$ and $R_{41}$ may be mutually the same or different and each are selected from a group consisting of halogen, a hydrogen atom, substituted or unsubstituted alkyl, substituted or unsubstituted aryl and a substituted or unsubstituted heterocyclic group. X represents a carbon atom or a nitrogen atom on a condition that $R_{39}$ above does not exist when X represents a nitrogen atom.

According to the present invention, the compound having the pyrromethene skeleton represented by the formula (2-1) or the metal complex of the compound is preferably a metal complex having a pyrromethene skeleton represented by the following formula (2-3).

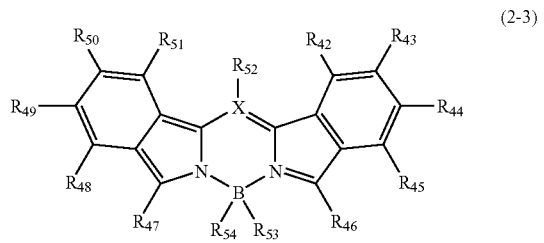

(2-3)

In the formula (2-3), $R_{42}$ to $R_{52}$ each represent a hydrogen atom, an alkyl group, a cycloalkyl group, an aralkyl group, an alkenyl group, a cycloalkenyl group, an alkynyl group, a hydroxyl group, a mercapto group, an alkoxy group, an alkylthio group, an arylether group, an arylthioether group, an aryl group, a heterocyclic group, halogen, haloalkane, haloalkene, haloalkyne, a cyano group, an aldehyde group, a carbonyl group, a carboxyl group, an ester group, a carbamoyl group, an amino group, a nitro group, a silyl group or a siloxanyl group. $R_{42}$ to $R_{52}$ may be mutually the same or different and may be substituted or unsubstituted. $R_{53}$ and $R_{54}$ may be mutually the same or different and each are selected from a group consisting of halogen, a hydrogen atom, a substituted or unsubstituted alkyl, a substituted or unsubstituted aryl and a substituted or unsubstituted heterocyclic group. X represents a carbon atom or a nitrogen atom on a condition that $R_{52}$ above does not exist when X represents a nitrogen atom.

Examples of the aromatic compound represented by the general formula (2) according to the present invention will be shown below. However, the present invention is not limited to the exemplary compounds shown below.

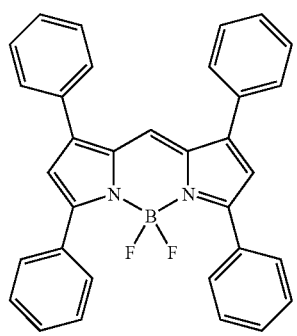

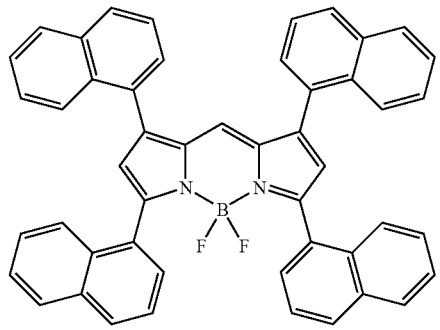

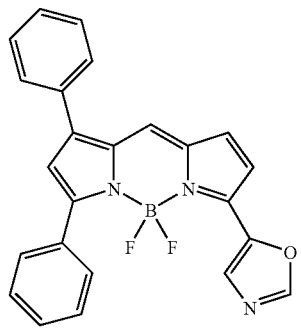

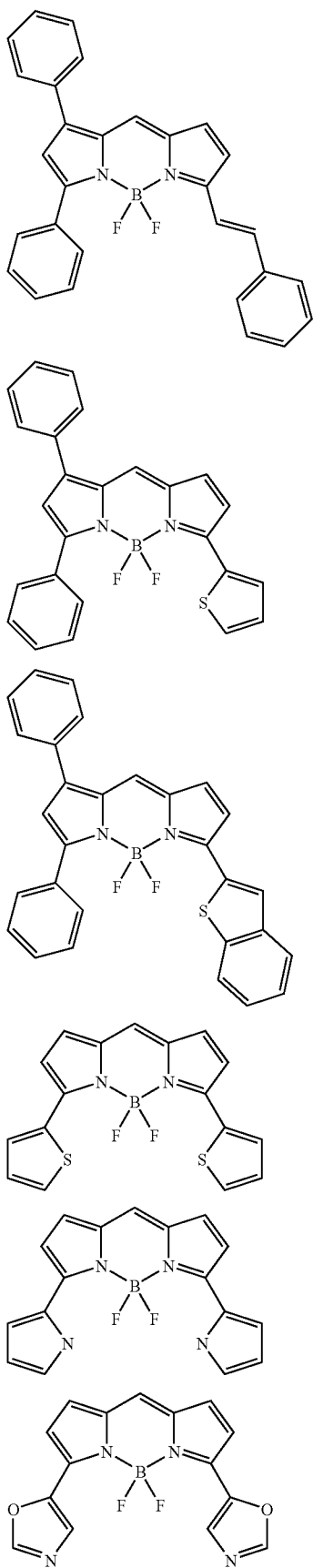
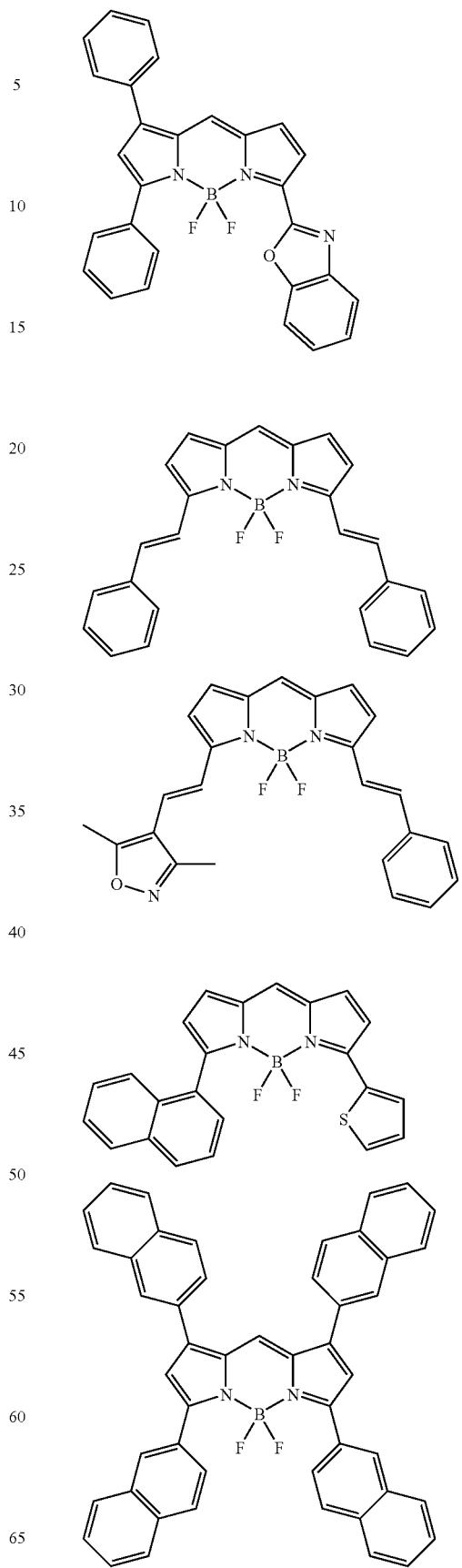

-continued
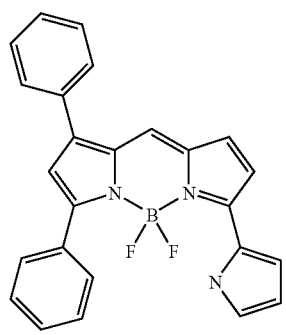
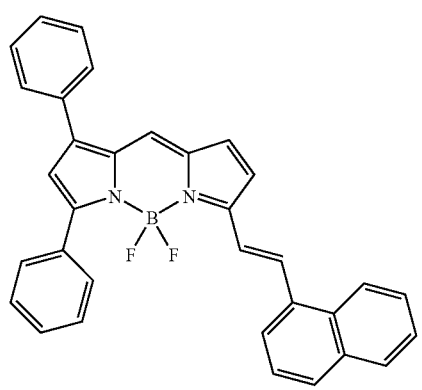
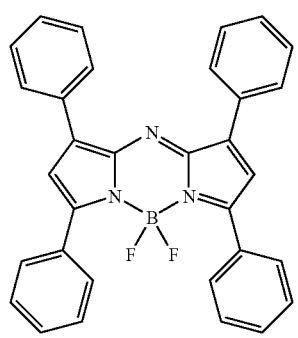
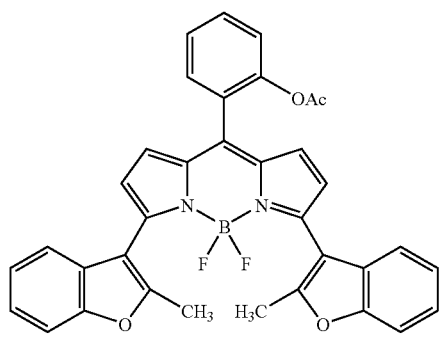
-continued
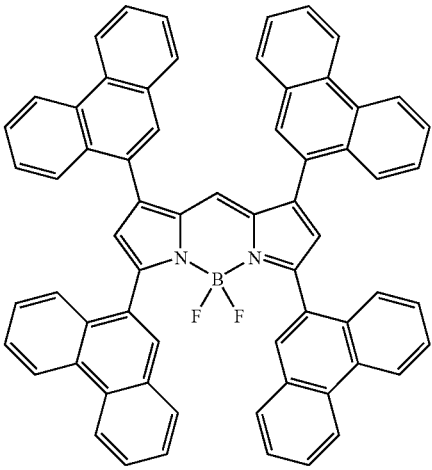
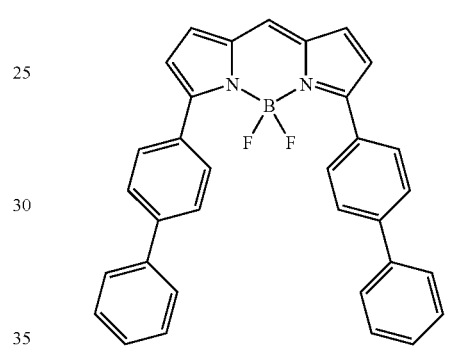
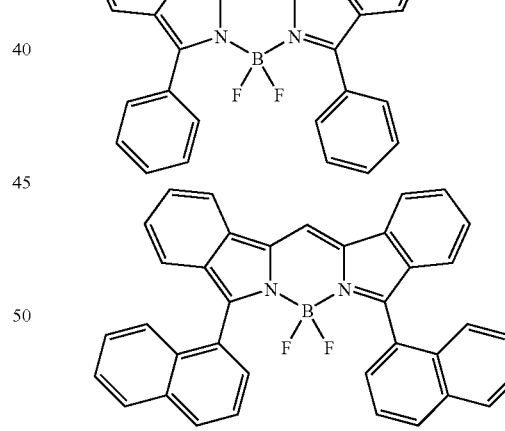
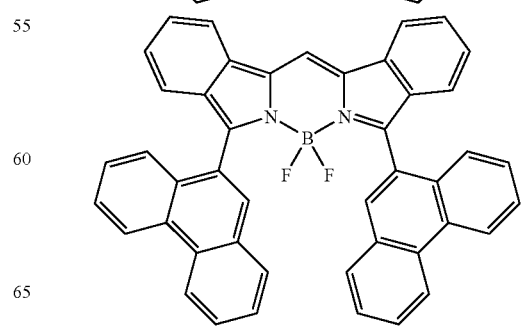

27
-continued
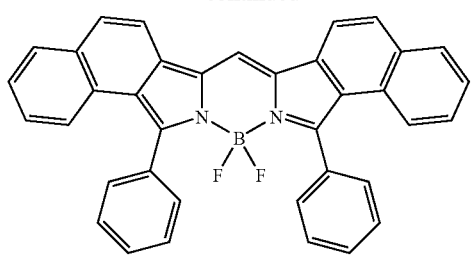
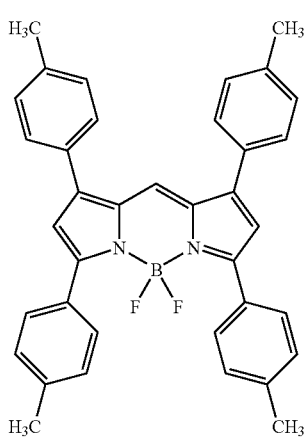
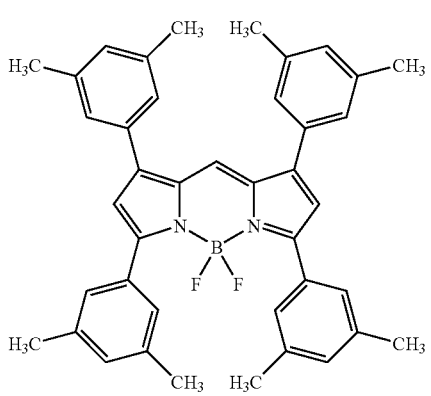
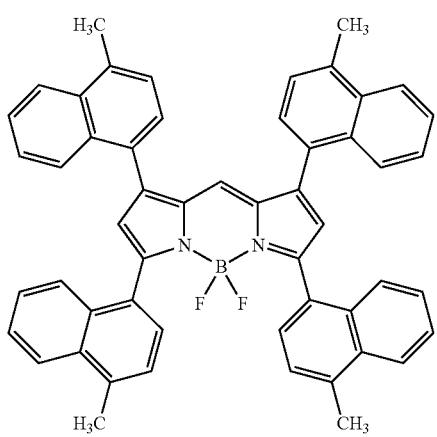
28
-continued
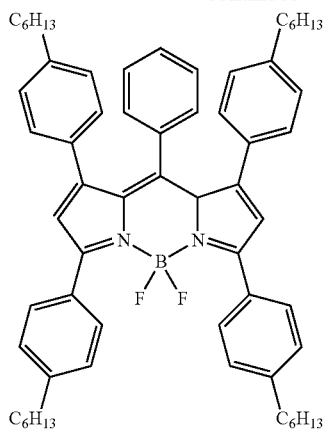
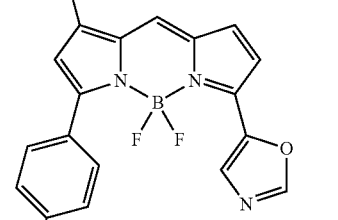
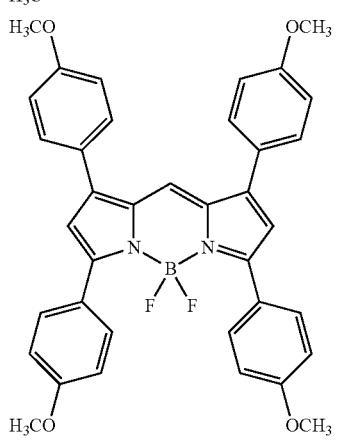
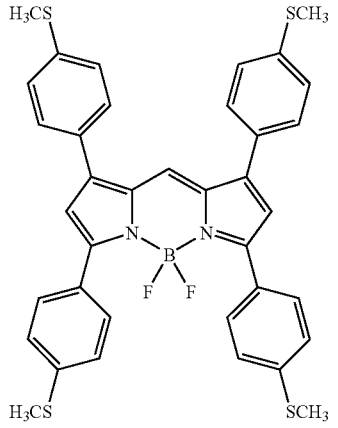

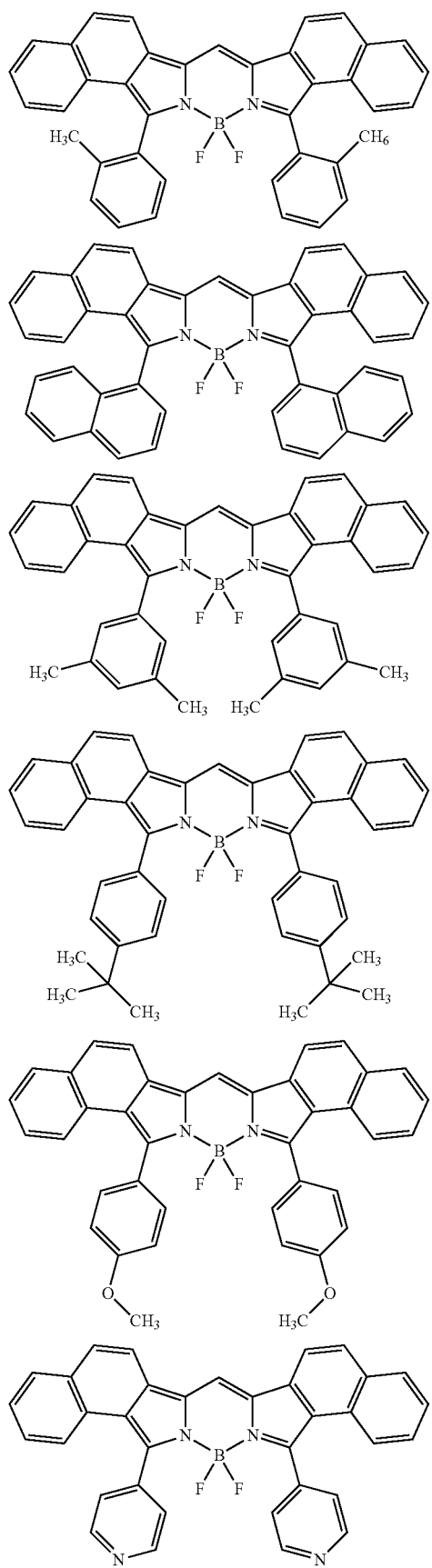
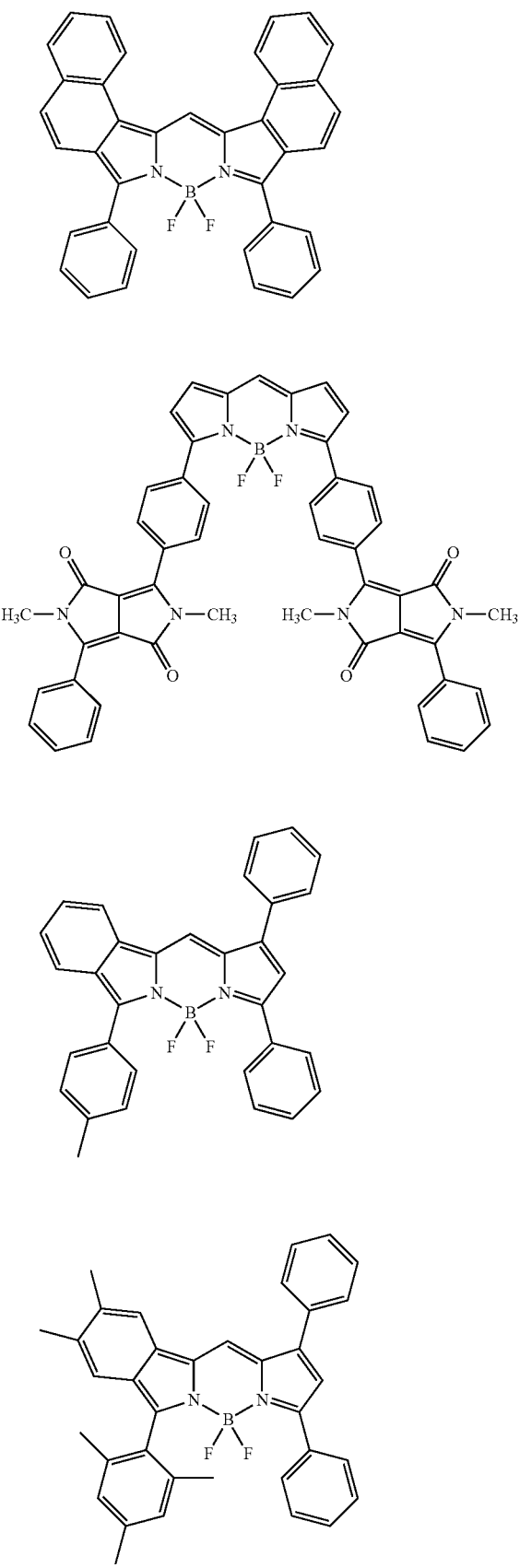

31
-continued
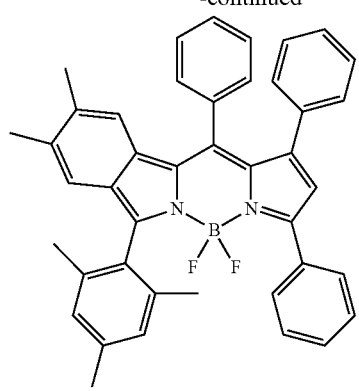
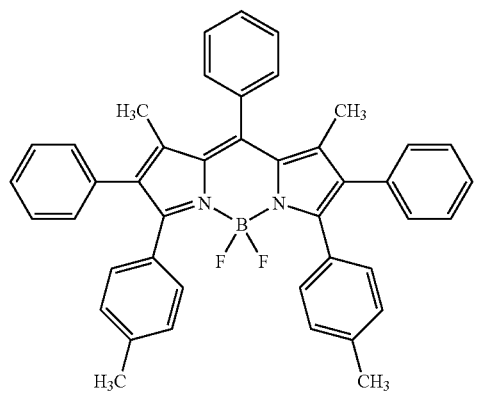
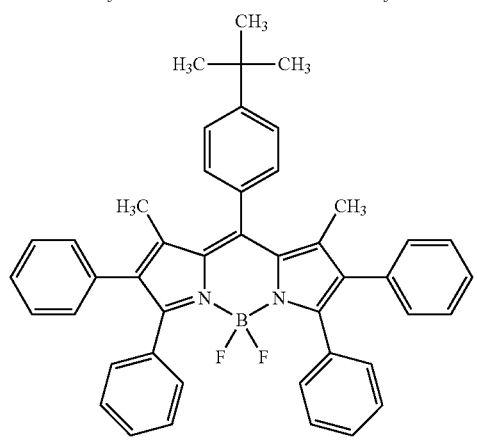
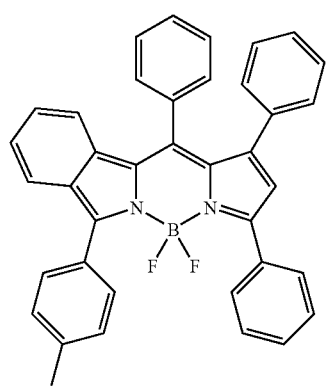
32
-continued
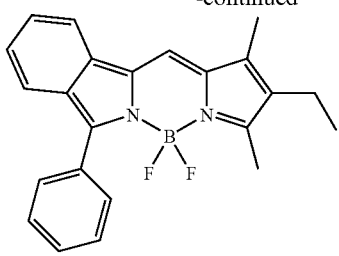
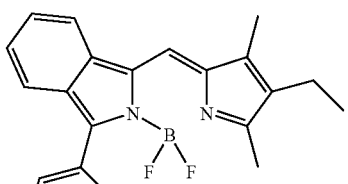
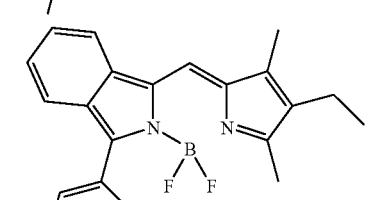
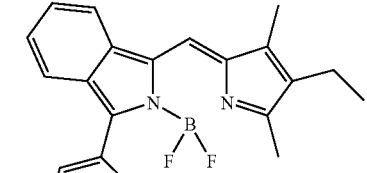
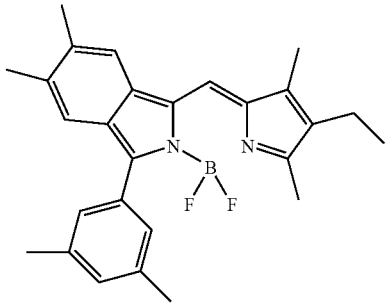
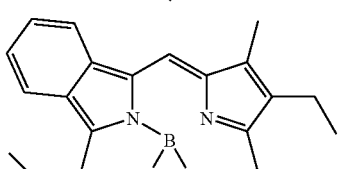
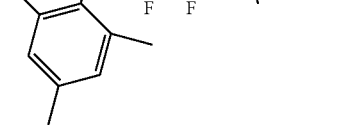

33
-continued
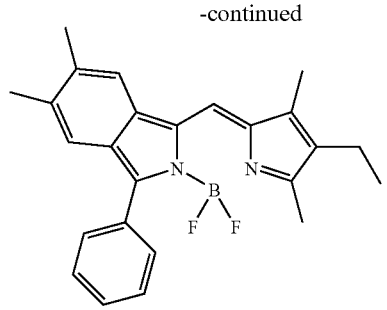
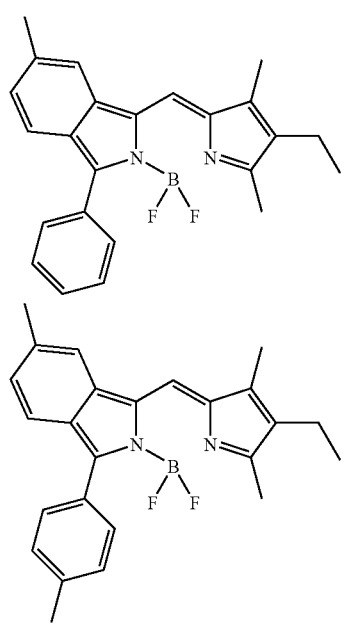
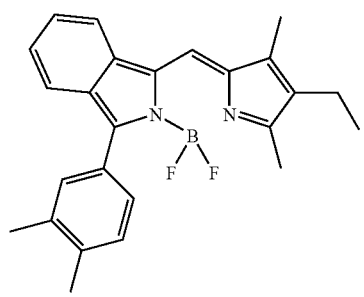
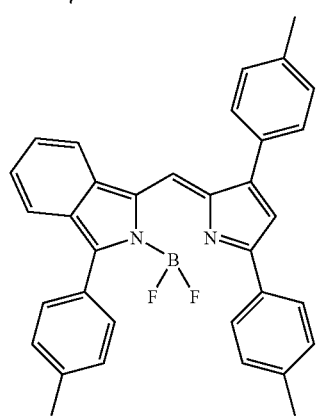
34
-continued
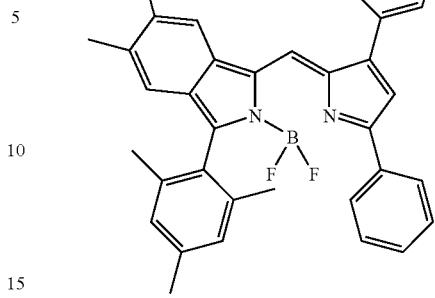
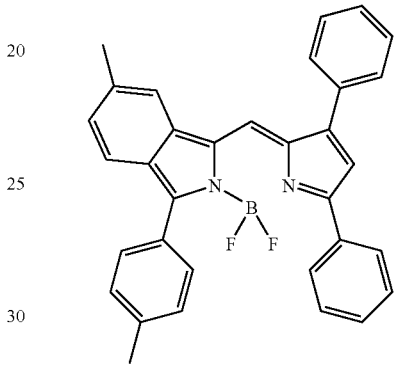
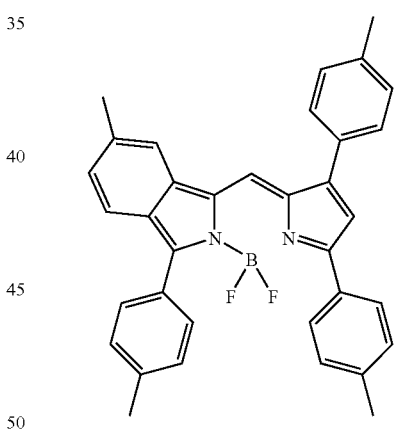
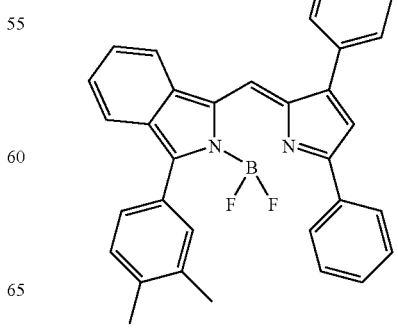

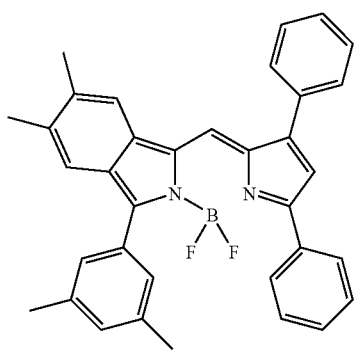
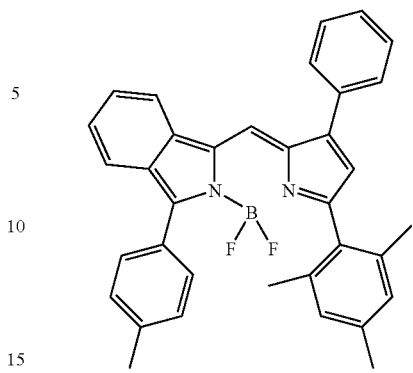
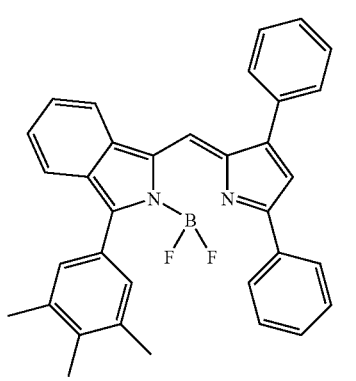
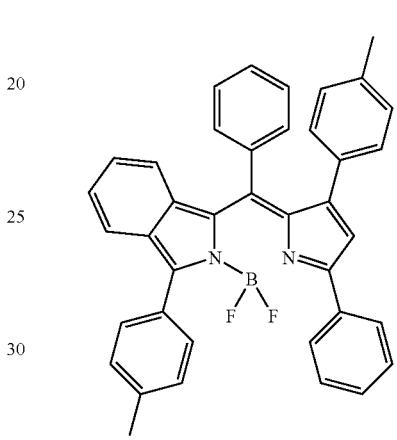
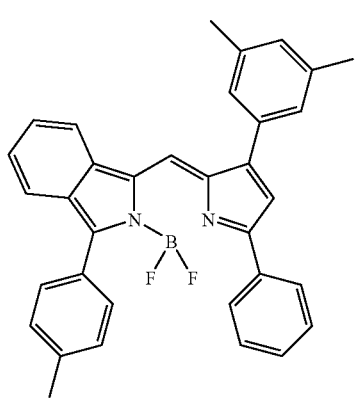
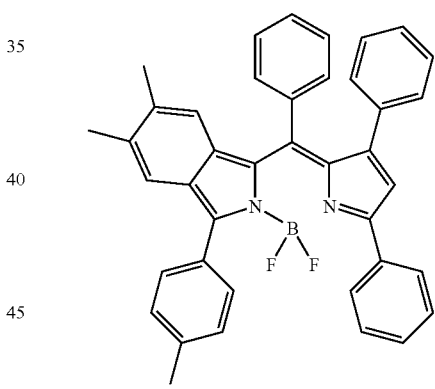
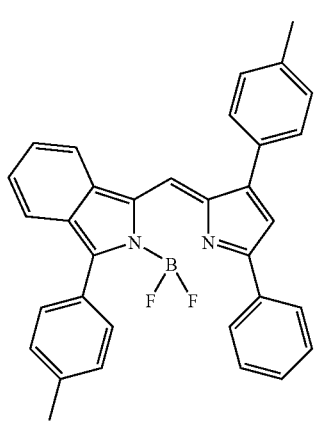
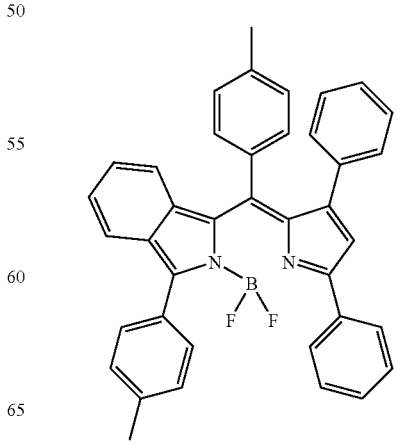

-continued
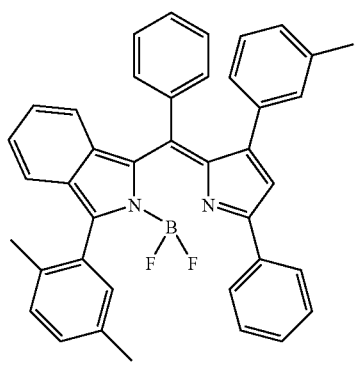
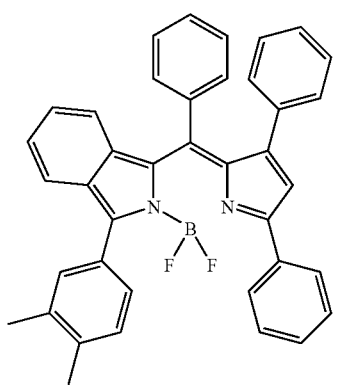
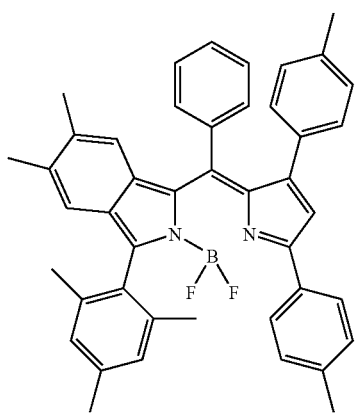
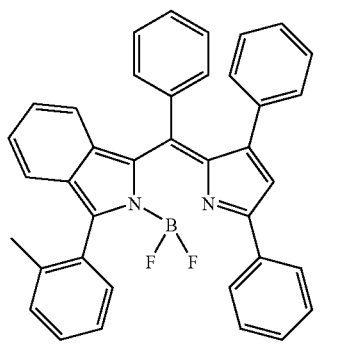
-continued
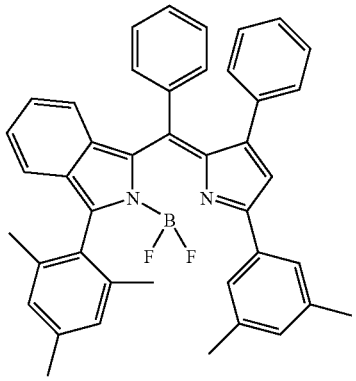
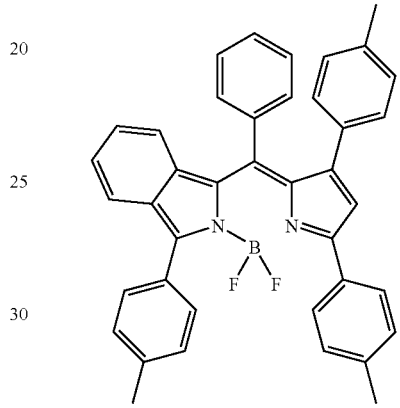
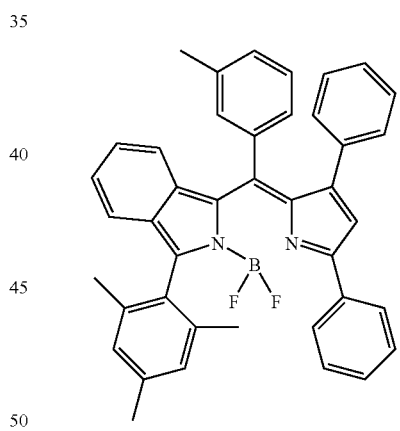
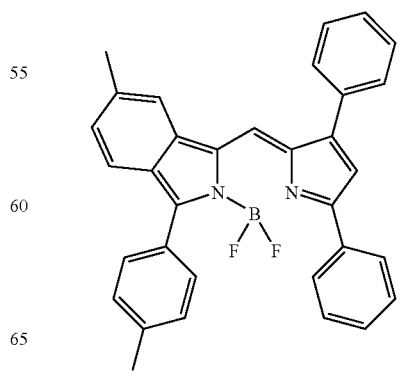

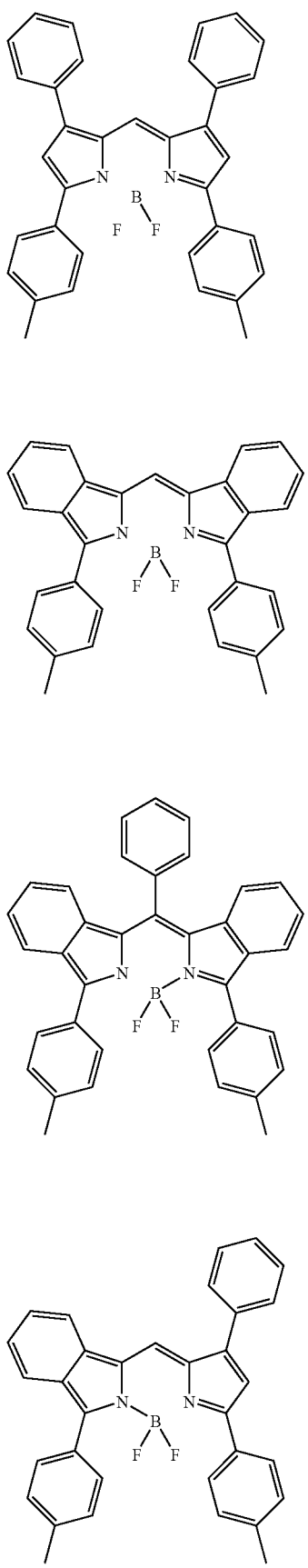
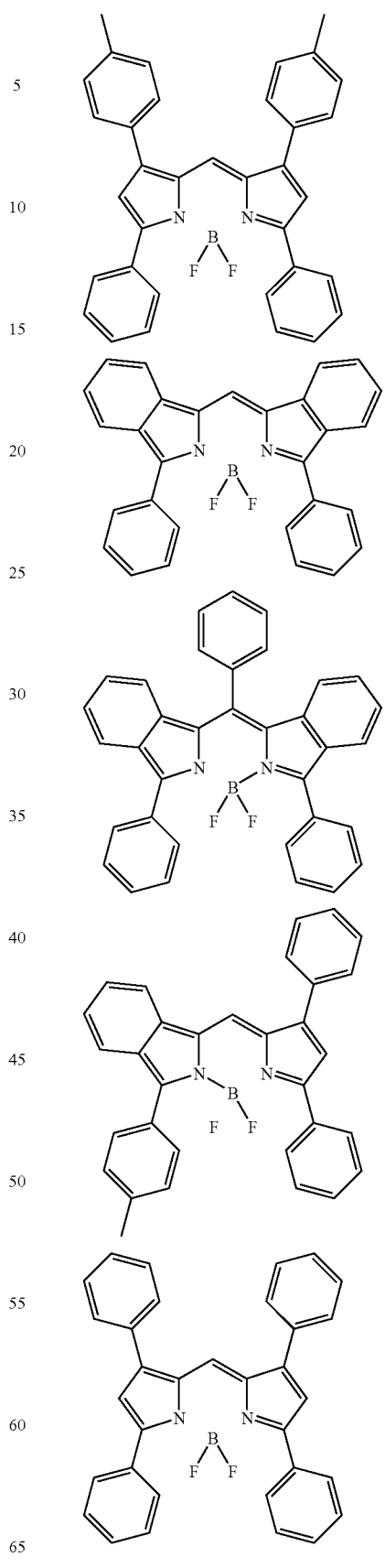

41
-continued
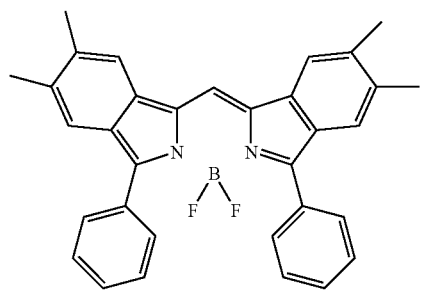
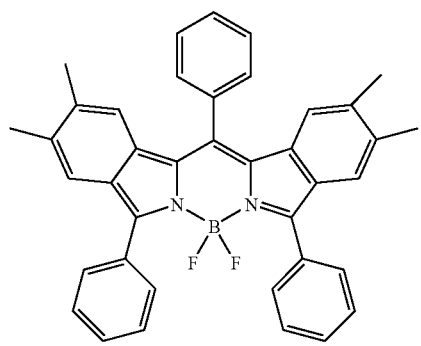
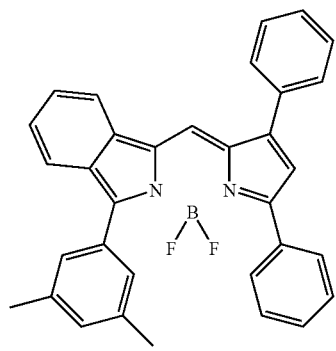
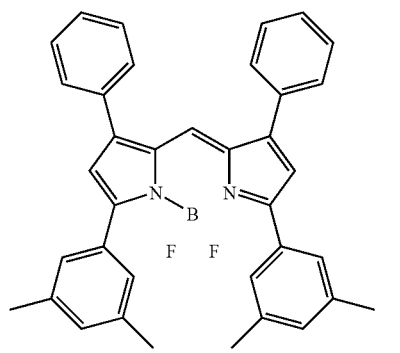
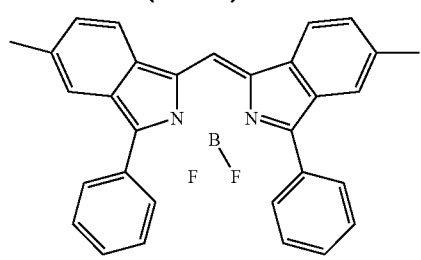
42
-continued
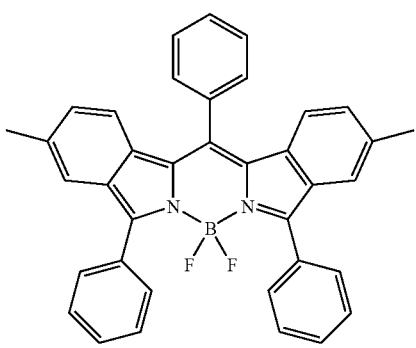
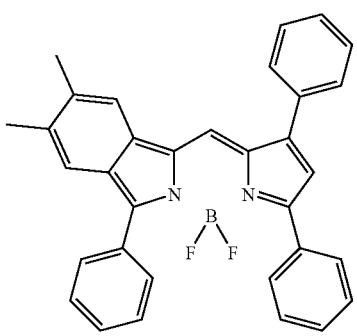
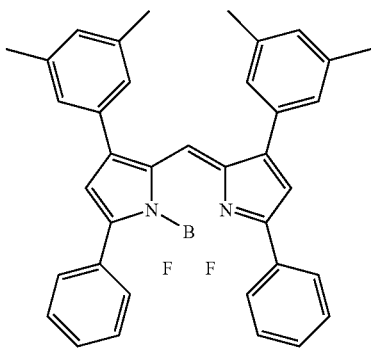
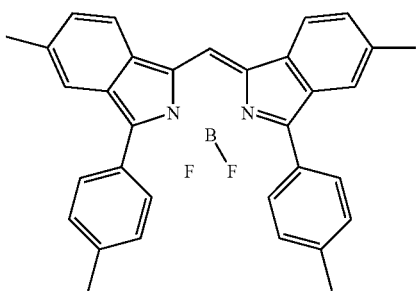
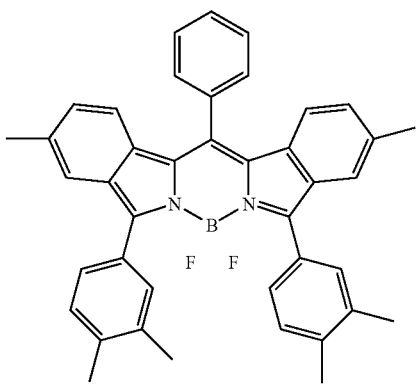

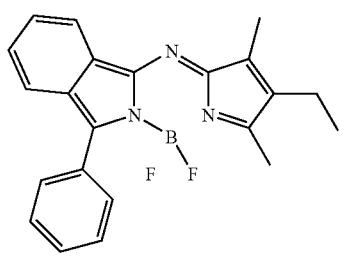
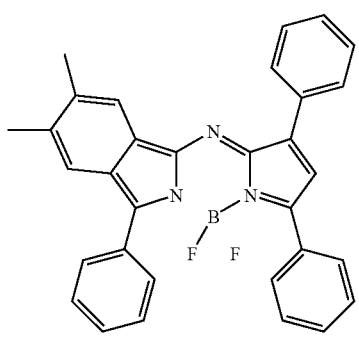
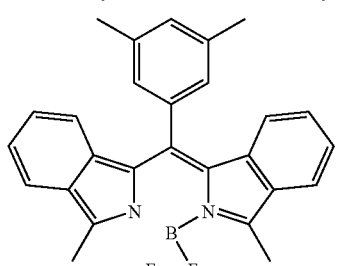
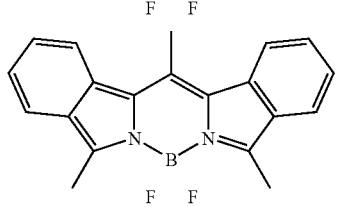
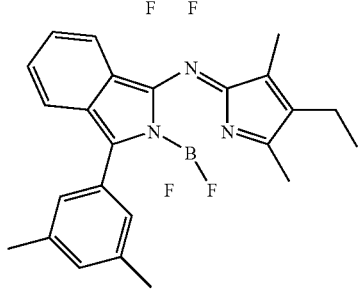
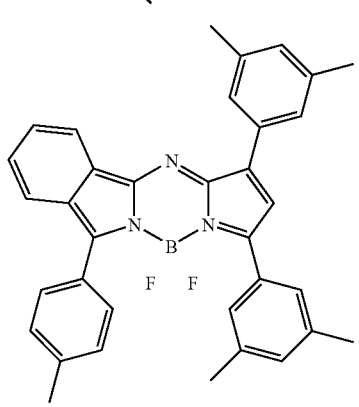
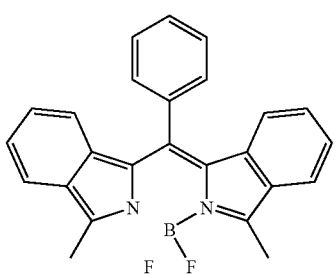
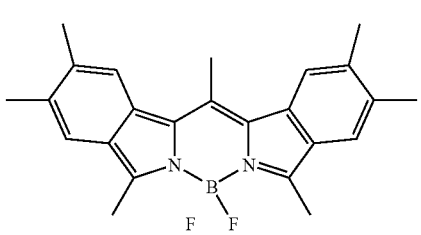
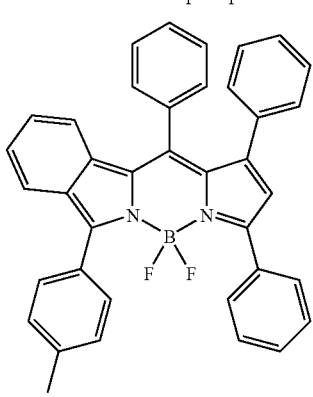
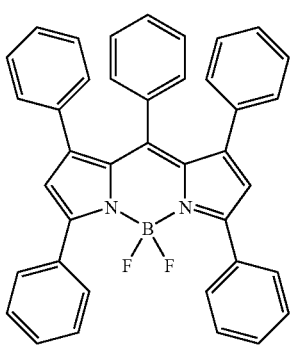
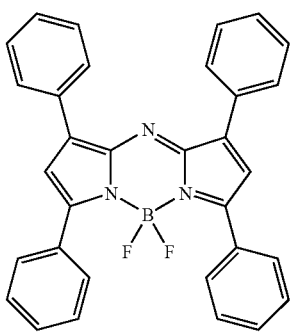

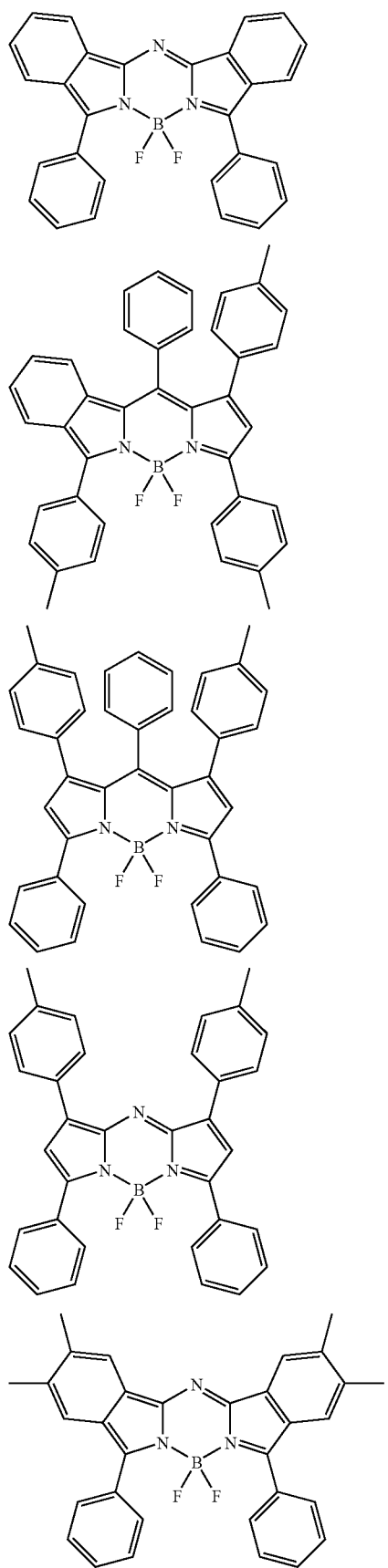
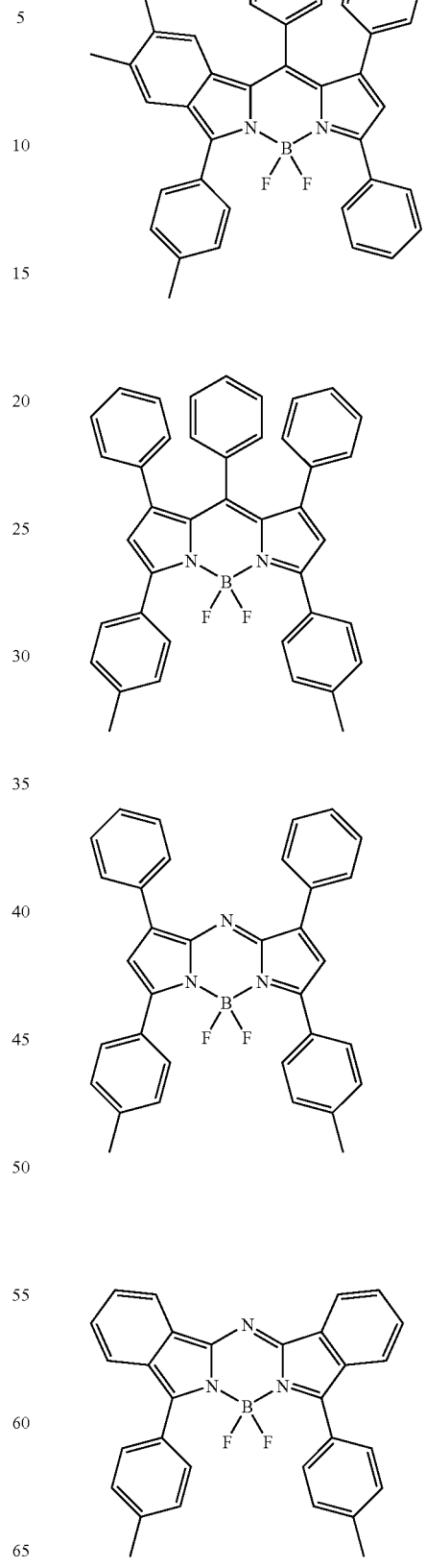

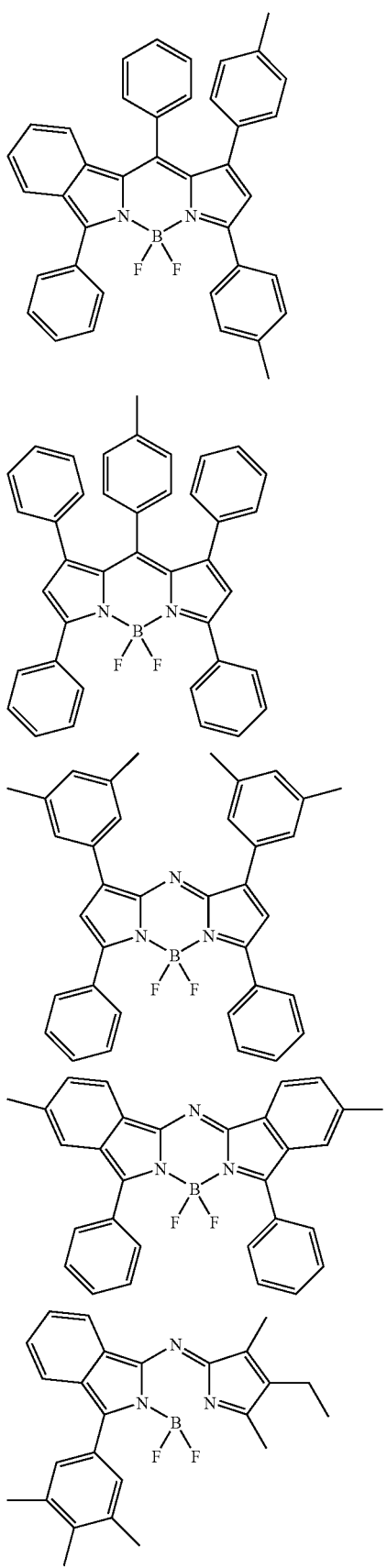
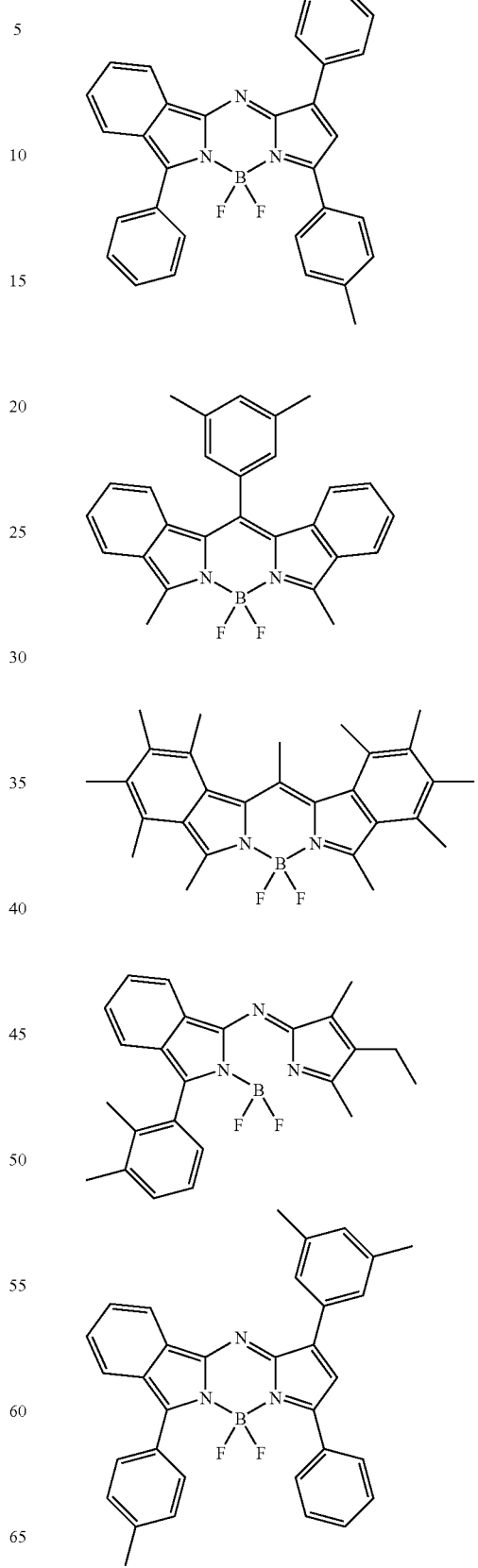

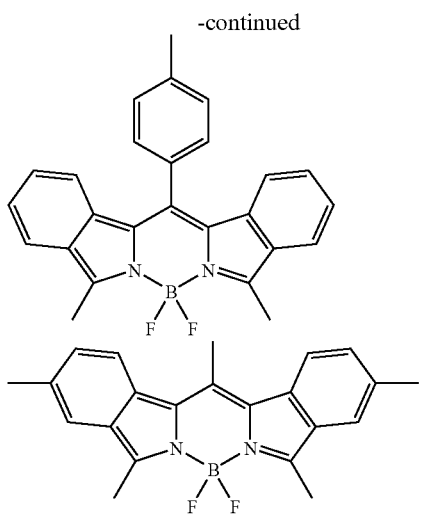

In the above formulae, $Q^{10}$ to $Q^{140}$ and $R^{15}$ to $R^{54}$ may be substituted or unsubstituted, a substituent for each of which is preferably an alkyl group, an aryl group or an alkoxy group.

The alkyl group is preferably an alkyl group having 1 to 20 carbon atoms, more preferably an alkyl group having 1 to 10 carbon atoms, further preferably an alkyl group having 1 to 5 carbon atoms. The alkyl group may be linear or branched. The alkyl group may be a primary alkyl group, a secondary alkyl group or a tertiary alkyl group.

Preferable examples of the alkyl group are a methyl group, an ethyl group, an n-propyl group, an isopropyl group, an n-butyl group, a sec-butyl group, a tert-butyl group, an n-pentyl group, an n-hexyl group, an n-heptyl group, an n-octyl group, an n-nonyl group and an n-decyl group.

The aryl group is preferably an aryl group having 6 to 30 carbon atoms, more preferably an aryl group having 6 to 20 carbon atoms. Examples of the aryl group are a phenyl group, a tolyl group, a xylyl group, a phenylphenyl group (4-phenylphenyl group, 3-phenylphenyl group, 2-phenylphenyl group), a naphthylphenyl group, a naphthyl group (1-naphthyl group, 2-naphthyl group), a phenylnaphthyl group, a naphthylnaphthyl group, a taphenyl group, an anthranil group, a phenantyl group, a pyrenyl group and a chrysenyl group.

[Hole Transporting Layer and Hole Injecting Layer]

The hole transporting layer helps injection of the holes into the emitting layer and transports the holes to an emitting region, in which the hole mobility is large and the energy of ionization is typically small (5.5 eV or smaller). A material of the hole transporting layer is preferably such a material that transports the holes to the emitting layer with a low field intensity, and more preferably such a material that transports the holes with the hole mobility of at least $10^{-4}$ cm$^2$/V*sec when the exemplary electrical field of $10^4$ to $10^6$ V/cm is applied.

A material for the hole transporting layer is not specifically limited as long as the material has the above preferable characteristics. Any materials conventionally used for transporting charges of the holes in photoconducting materials or any materials publicly known to be applicable to the hole transporting layers of the EL devices may be used.

Examples of the material are a triazole derivative (see, for instance, the specification of U.S. Pat. No. 3,112,197), an oxadiazole derivative (see, for instance, the specification of U.S. Pat. No. 3,189,447), an imidazole derivative (see, for instance, the publication of JP-B-37-16096), a polyarylalkane derivative (see, for instance, the specifications of U.S. Pat. No. 3,615,402, U.S. Pat. No. 3,820,989 and U.S. Pat. No. 3,542,544 and the publications of JP-B-45-555, JP-B-51-10983, JP-A-51-93224, JP-A-55-17105, JP-A-56-4148, JP-A-55-108667, JP-A-55-156953, and JP-A-56-36656), a pyrazoline derivative and a pyrazolone derivative (see, for instance, the specifications of U.S. Pat. No. 3,180,729 and U.S. Pat. No. 4,278,746 and the publications of JP-A-55-88064, JP-A-55-88065, JP-49-105537, JP-A-55-51086, JP-A-56-80051, JP-A-56-88141, JP-A-57-45545, JP-A-54-112637 and JP-A-55-74546, a phenylenediamine derivative (see, for instance, the specification of U.S. Pat. No. 3,615,404 and the publications of JP-B-51-10105, JP-B-46-3712, JP-B-47-25336 and JP-A-54-119925), an arylamine derivative (see, for instance, the specifications of U.S. Pat. No. 3,567,450, U.S. Pat. No. 3,240,597, U.S. Pat. No. 3,658,520, U.S. Pat. No. 4,232,103, U.S. Pat. No. 4,175,961 and U.S. Pat. No. 4,012,376 and the publications of JP-B-49-35702, JP-B-39-27577, JP-A-55-144250, JP-A-56-119132 and JP-A-56-22437 and the specification of West Germany Patent No. 1,110,518), an amino-substituted chalcone derivative (see, for instance, the specification of U.S. Pat. No. 3,526,501), an oxazole derivative (disclosed in, for instance, the specification of U.S. Pat. No. 3,257,203), a styrylanthracene derivative (see, for instance, the publication of JP-A-56-46234), a fluorenone derivative (see, for instance, the publication of JP-A-54-110837), a hydrazone derivative (see, for instance, the specification of U.S. Pat. No. 3,717,462 and the publications of JP-A-54-59143, JP-A-55-52063, JP-A-55-52064, JP-A-55-46760, JP-A-57-11350, JP-A-57-148749 and JP-A-2-311591), a stilbene derivative (see, for instance, the publications of JP-A-61-210363, JP-A-61-228451, JP-A-61-14642, JP-A-61-72255, JP-A-62-47646, JP-A-62-36674, JP-A-62-10652, JP-A-62-30255, JP-A-60-93455, JP-A-60-94462, JP-A-60-174749 and JP-A-60-175052), a silazane derivative (see the specification of U.S. Pat. No. 4,950,950), a polysilane type (see the publication of JP-A-2-204996), an aniline-based copolymer (see the publication of JP-A-02-282263), and a conductive high-molecular oligomer (particularly, thiophene oligomer).

Preferably, a material represented by the following formula (7) may be used.

$$Q^1\text{-}G\text{-}Q^2 \qquad (7)$$

In the formula (7), $Q^1$ and $Q^2$ each represent a portion having at least one tertiary amine while G represents a linking group.

More preferable material is an amine derivative represented by the following formula (8).

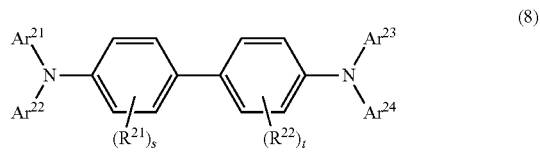

In the above formula (8), $Ar^{21}$ to $Ar^{24}$ each represent a substituted or unsubstituted aromatic ring having 6 to 50 carbon atoms forming the ring or a substituted or unsubstituted heteroaromatic ring having 5 to 50 atoms forming the ring. $R^{21}$ and $R^{22}$ each represent a substituent while s and t each represent an integer in a range of 0 to 4. $Ar^{21}$ and $Ar^{22}$ may be bonded together to form a cyclic structure while $Ar^{23}$ and Ar$^{24}$ may also be bonded together to form a cyclic structure. R$^{21}$ and R$^{22}$ may also be bonded together to form a cyclic structure.

The substituent for Ar$^{21}$ to Ar$^{24}$ each, and R$^{21}$ and R$^{22}$ are selected from a group consisting of a substituted or unsubstituted aromatic ring having 6 to 50 carbon atoms forming the ring, a substituted or unsubstituted heteroaromatic ring having 5 to 50 atoms forming the ring, an alkyl group having 1 to 50 carbon atoms, an alkoxy group having 1 to 50 carbon atoms, an alkylaryl group having 1 to 50 carbon atoms, an aralkyl group having 1 to 50 carbon atoms, a styryl group, an amino group substituted by an aromatic ring having 6 to 50 carbon atoms forming the ring or by a heteroaromatic ring having 5 to 50 atoms forming the ring, an aromatic ring having 6 to 50 carbon atoms forming the ring substituted by an amino group substituted by an aromatic ring having 6 to 50 carbon atoms forming the ring or by a heteroaromatic ring having 5 to 50 atoms forming the ring, and a heteroaromatic ring having 5 to 50 atoms forming the ring substituted by an amino group substituted by an aromatic ring having 6 to 50 carbon atoms forming the ring or by a heteroaromatic ring having 5 to 50 atoms forming the ring.

In order to aid the injection of the holes, a hole injecting layer may be provided in addition to the hole transporting layer. The above materials for the hole transporting layer can be used as the materials of the hole injecting layer, preferable examples of which are a porphyrin compound (disclosed in JP-A-63-295695), an aromatic tertiary amine compound and a styrylamine compound (see, for instance, the specification of U.S. Pat. No. 4,127,412, JP-A-53-27033, JP-A-54-58445, JP-A-55-79450, JP-A-55-144250, JP-A-56-119132, JP-A-61-29558, JP-A-61-98353 and JP-A-63-295695). Among these, use of an aromatic tertiary amine compound is particularly preferable.

In addition, 4,4'-bis(N-(1-naphthyl)-N-phenylamino)biphenyl (hereinafter, abbreviated as NPD) having in the molecule two condensed aromatic rings disclosed in U.S. Pat. No. 5,061,569, 4,4',4''-tris(N-3-methylphenyl-N-phenylamino)triphenylamine (hereinafter, abbreviated as MTDATA) in which three triphenylamine units disclosed in JP-A-04-30868 are bonded in a starbust form and the like may also be used.

As another example, a nitrogen-containing heterocyclic derivative represented by the following formula (9), which is disclosed in Japanese Patent No. 03571977, may be used.

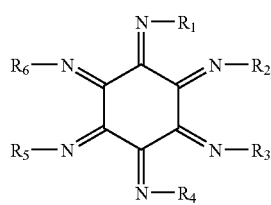

(9)

In the formula (9), R$_1$ to R$_6$ each represent a substituted or unsubstituted alkyl group, a substituted or unsubstituted aryl group, a substituted or unsubstituted aralkyl group, or a substituted or unsubstituted heterocyclic group. R$_1$ to R$_6$ may be mutually the same or different. A pair of R$_1$ and R$_2$, a pair of R$_3$ and R$_4$ or a pair of R$_5$ and R$_6$ may form a condensed ring(s). Alternatively, a pair of R$_1$ and R$_6$, a pair of R$_2$ and R$_3$ or a pair of R$_4$ and R$_5$ may form a condensed ring(s).

As another example, a compound represented by the following formula (10), which is disclosed in US 2004/113547A1, may be used.

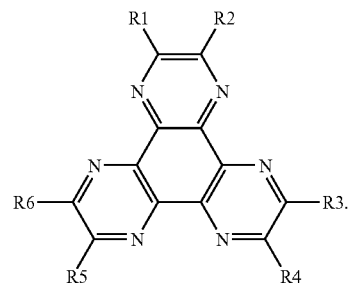

(10)

In the formula (10), R1 to R6 each represent a substituent, a preferable example of which is an electron-attracting group such as a cyano group, a nitro group, a sulfonyl group, a carbonyl group, a trifluoromethyl group and halogen.

In addition to aromatic dimethylidyne-based compounds, inorganic compounds such as p-type Si and p-type SiC can be used as the material of the hole injecting layer.

The hole injecting layer and the hole transporting layer can be formed by forming thin films from the compounds listed above by known methods such as vacuum deposition, spin coating, casting and the LB method. Although the thickness of the hole injecting layer and the hole transporting layer is not particularly limited, the thickness is typically in the range from 5 nm to 5 μm. The hole injecting layer and the hole transporting layer may be formed by a single layer formed of at least one of the above materials as long as the hole injecting layer and the hole transporting layer contains the above compound(s) in the hole transporting region. Alternatively, the hole injecting layer and the hole transporting layer may be formed by laminating layers respectively formed of a different material.

In addition, an organic semiconductor layer, which is a part of the hole transporting layer, aids the injection of the holes or the electrons into the emitting layer. The organic semiconductor layer preferably has electric conductivity of $10^{-10}$ S/cm or more. Examples of a material for the organic semiconductor layer are a conductive oligomer such as a thiophene-containing oligomer or an arylamine-containing oligomer (disclosed in JP-A-08-193191), and a conductive dendrimer such as an arylamine-containing dendrimer.

[Electron Injecting/Transporting Layers (Electron Transport Zone)]

The electron transporting layer, which aids injection of the electrons into the emitting layer, has a high electron mobility. The thickness of the electron transporting layer is suitably selected from the range of several nanometers to several micrometers. However, especially when the thickness of the electron transporting layer is large, the electron mobility, in order to prevent voltage from rising, is preferably at least $10^{-5}$ cm$^2$/Vs or higher with the electrical field of $10^4$ to $10^6$ V/cm applied.

The electron transporting layer preferably contains a compound represented by any one of the following formulae (4), (5) and (6).

In the formulae (5) and (6), R represents a hydrogen atom, a substituted or unsubstituted aryl group having 6 to 60 carbon atoms, a substituted or unsubstituted pyridyl group, substituted or unsubstituted quinolyl group, a substituted or unsubstituted alkyl group having 1 to 20 carbon atoms, or a substituted or unsubstituted alkoxy group having 1 to 20 carbon atoms while p represents an integer in a range of 1 to 4.

Preferable examples of the aryl group having 6 to 60 carbon atoms are a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-ta-phenyl-4-yl group, p-ta-phenyl-3-yl group, p-ta-phenyl-2-yl group, m-ta-phenyl-4-yl group, m-ta-phenyl-3-yl group, m-ta-phenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-ta-phenyl-4-yl group, fluoranthenyl group and fluorenyl group. More preferable examples thereof are a phenyl group, naphthyl group, biphenyl group, anthracenyl group, phenanthryl group, pyrenyl group, crycenyl group, fluoranthenyl group and fluorenyl group.

Preferable examples of the alkyl group having 1 to 20 carbon atoms are a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobuthyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbornyl group and 2-norbornyl group.

The alkoxy group having 1 to 20 carbon atoms is a group represented by —OY'". Examples of Y'" are the same as those of the above alkyl group.

Examples of the substituent for the aryl group, the pyridyl group, the quinolyl group, the alkyl group or the alkoxy group are a substituted or unsubstituted aryl group having 6 to 50 carbon atoms forming the ring, a substituted or unsubstituted aromatic heterocyclic group having 5 to 50 atoms forming the ring, a substituted or unsubstituted alkyl group having 1 to 50 carbon atoms, a substituted or unsubstituted alkoxy group having 1 to 50 carbon atoms, a substituted or unsubstituted aralkyl group having 1 to 50 carbon atoms, a substituted or unsubstituted aryloxy group having 5 to 50 atoms forming the ring, a substituted or unsubstituted arylthio group having 5 to 50 atoms forming the ring, a substituted or unsubstituted carboxyl group having 1 to 50 carbon atoms, a halogen group, a cyano group, a nitro group and a hydroxyl group.

In the formulae (5) and (6), p represents an integer in a range of 1 to 4. Preferably, p is any one of 1 to 3, more preferably 1 or 2.

R preferably represents a hydrogen atom.

$R^{11}$ represents a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms or an alkoxy group having 1 to 20 carbon atoms. Examples of each group and substituent are the same as R.

$R^{12}$ represents a hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms or a substituted or unsubstituted alkoxy group having 1 to 20 carbon atoms. Examples of each group and substituent are the same as R.

L represents a substituted or unsubstituted arylene group having 6 to 60 carbon atoms, a substituted or unsubstituted pyridinylene group, a substituted or unsubstituted quinolinylene group, or a substituted or unsubstituted fluorenylene group.

Preferable examples of the arylene group having 6 to 60 carbon atoms are divalent substituents formed by further removing one hydrogen atom from the substituents listed in the description of the aryl group having 6 to 60 carbon atoms. More preferable examples thereof are a phenylene group, naphthylene group, biphenylene group, anthracenylene group, phenantolylene group, pyrenylene group, chrysenylene group, fluoranthenylene group and fluorenylene group.

Examples of the substituent for each of the arylene group, the pyridinylene group, the quinolinylene group or the fluorenylene group are the same as R.

$Ar^1$ represents a substituted or unsubstituted aryl group having 6 to 60 carbon atoms (preferably, 6 to 30 carbon atoms), a substituted or unsubstituted pyridyl group or a substituted or unsubstituted quinolyl group.

Examples of the substituent for each of the aryl group having 6 to 60 carbon atoms, the aryl group, the pyridyl group or the quinolyl group are the same as R.

Preferably in the benzoimidazole derivative represented by the formula (5): R represents a hydrogen atom; $R^{11}$ represents an aryl group; L represents an arylene group having 6 to 30 carbon atoms (preferably, 6 to 20 carbon atoms); and $Ar^1$ represents an aryl group having 6 to 30 carbon atoms.

Preferably in the benzoimidazole derivative represented by the formula (6): R represents a hydrogen atom; $R^{12}$ represents an aryl group; L represents an arylene group having 6 to 30 carbon atoms (preferably, 6 to 20 carbon atoms); and $Ar^1$ represents an aryl group having 6 to 30 carbon atoms.

Although the compound(s) represented by the formulae (4), (5) and (6) are preferably applicable to the electron transporting layer, the material of the electron transporting layer is not limited thereto. Compounds containing 8-hydroxyquinoline, a metal complex of its derivative, or a nitrogen-containing heterocycle may be preferably applicable to the electron transporting layer.

An example of the 8-hydroxyquinoline or the metal complex of its derivative is a metal chelate oxinoid compound containing a chelate of oxine (typically 8-quinolinol or 8-hydroxyquinoline). For example, an Alq complex having Al as its central metal can be used for the electron transporting layer.

On the other hand, examples of the oxadiazole derivative are electron transporting compounds represented by the following general formulae.

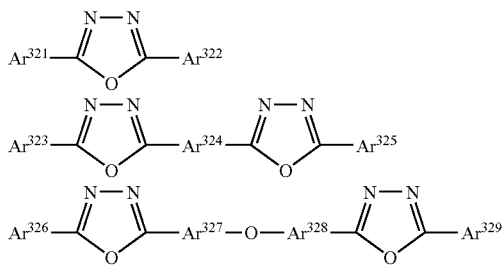

In the formulae, $Ar^{321}$, $Ar^{322}$, $Ar^{323}$, $Ar^{325}$, $Ar^{326}$ and $Ar^{329}$ each represent a substituted or unsubstituted aryl group, which may be mutually the same or different. $Ar^{324}$, $Ar^{327}$ and $Ar^{328}$ each represent a substituted or unsubstituted arylene group, which may be mutually the same or different.

Examples of the aryl group are a phenyl group, a biphenyl group, an anthranil group, a perylenyl group, and a pyrenyl group. Examples of the arylene group are a phenylene group, a naphthylene group, a biphenylene group, an anthranylene group, a perylenylene group and a pyrenylene group. Examples of the substituent therefor are an alkyl group having 1 to 10 carbon atoms, an alkoxy group having 1 to 10 carbon atoms or a cyano group. The electron transporting compounds are preferably compounds that exhibit favorable performance in forming a thin film.

Examples of the electron transporting compounds are as follows.

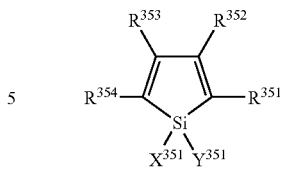

In the formula, $X^{351}$ and $Y^{351}$ may each represent a saturated or unsaturated hydrocarbon group having 1 to 6 carbon atoms, an alkoxy group, an alkenyloxy group, an alkynyloxy group, a hydroxy group, a substituted or unsubstituted aryl group or a substituted or unsubstituted heterocycle, or $X^{351}$ and $Y^{351}$ may be bonded together to form a saturated or unsaturated ring. $R^{351}$ to $R^{354}$ may each represent hydrogen, halogen, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, and arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group or cyano group, or an

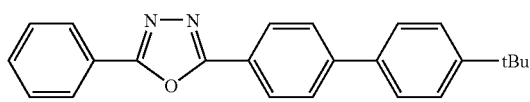

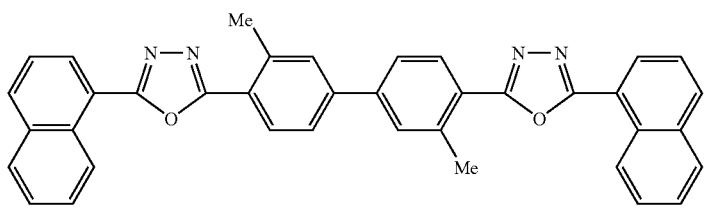

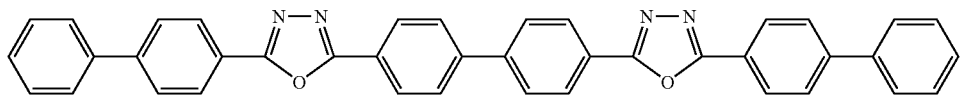

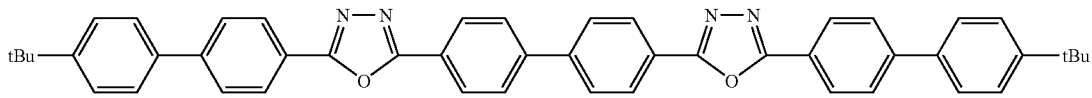

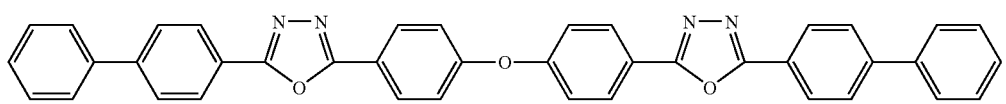

Me represents a methyl group while Bu represents a butyl group.

A silacyclopentadiene derivative represented by the following formula (disclosed in JP-A-09-087616) is also preferably applicable to the electron transporting layer.

adjacent set of $R^{351}$ to $R^{354}$ may be condensed to form a substituted or unsubstituted ring.

A silacyclopentadiene derivative represented by the following formula (disclosed in JP-A-09-194487) is also preferably applicable to the electron transporting layer.

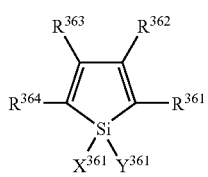

In the formula, $X^{361}$ and $Y^{361}$ may each represent a saturated or unsaturated hydrocarbon group having 1 to 6 carbon atoms, an alkoxy group, an alkenyloxy group, an alkynyloxy group, a substituted or unsubstituted aryl group or a substituted or unsubstituted heterocycle, or $X^{361}$ and $Y^{361}$ may be bonded together to form a saturated or unsaturated ring. $R^{361}$ to $R^{364}$ may each represent hydrogen, halogen, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group or cyano group, or an adjacent set of $R^{361}$ to $R^{364}$ may be condensed to form a substituted or unsubstituted ring. However, when $R^{361}$ and $R^{364}$ are phenyl groups, neither $X^{361}$ nor $Y^{361}$ is an alkyl group or a phenyl group. When $R^{361}$ and $R^{364}$ are thienyl groups, $X^{361}$ and $Y^{361}$ are each a univalent hydrocarbon group provided that neither $R^{362}$ nor $R^{361}$ is an alkyl group, an aryl group or an alkenyl group, or that $R^{362}$ and $R^{363}$ are not bonded together to form an aliphatic ring group. When $R^{361}$ and $R^{364}$ are silyl groups, none of $R^{362}$, $R^{363}$, $X^{361}$ and $Y^{361}$ is a univalent hydrocarbon group having 1 to 6 carbon atoms or a hydrogen atom. When $R^{361}$ and $R^{362}$ are of a condensed benzene-ring structure, neither of $X^{361}$ nor $Y^{361}$ is an alkyl group or a phenyl group.

A borane derivative represented by the following formula (disclosed in JP-A1-2000-040586) is also preferably applicable to the electron transporting layer.

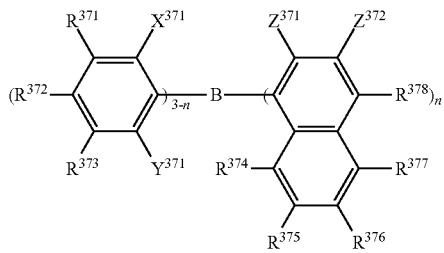

In the formula, $R^{371}$ to $R^{378}$ and $Z^{372}$ each represent a hydrogen atom, a saturated or unsaturated hydrocarbon group, an aromatic group, a heterocyclic group, a substituted amino group, a substituted boryl group, an alkoxy group or an aryloxy group; $X^{371}$, $Y^{371}$ and $Z^{371}$ each represent a saturated or unsaturated hydrocarbon group, an aromatic group, a heterocyclic group, a substituted amino group, an alkoxy group or an aryloxy group; substituent groups of $Z^{371}$ and $Z^{372}$ may be bonded to form a condensed ring; and n represents an integer in a range of 1 to 3, where when n is equal to or larger than 2, $Z^{371}$ does not have to be the same. However, the above does not apply when: n is 1; $X^{371}$, $Y^{371}$ and $R^{372}$ are the methyl groups; and $R^{378}$ is the hydrogen atom or the substituted boryl group, or when: n is 3; and $Z^{371}$ is the methyl group.

A compound represented by the following formula (disclosed in JP-A-10-088121) is also preferably applicable to the electron transporting layer.

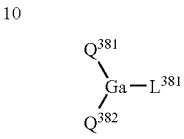

In this formula, $Q^{381}$ and $Q^{382}$ each represent a ligand shown by the formula below. $L^{381}$ represents a ligand which may be a halogen atom, a substituted or unsubstituted alkyl group, a substituted or unsubstituted cycloalkyl group, a substituted or unsubstituted aryl group, a substituted or unsubstituted heterocyclic group, or $L^{381}$ represents a ligand represented by —$OR^{391}$ ($R^{391}$ representing a hydrogen atom, a substituted or unsubstituted alkyl group, a substituted or unsubstituted cycloalkyl group, a substituted or unsubstituted aryl group or a substituted or unsubstituted heterocyclic group) or a ligand represented by —O—Ga-$Q^{391}$($Q^{392}$) ($Q^{391}$ and $Q^{392}$ being the same as $Q^{381}$ and $Q^{382}$).

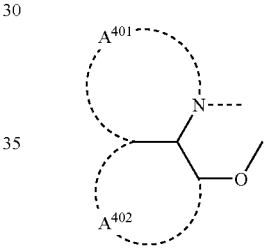

In the above formula, rings $A^{401}$ and $A^{402}$ are bonded together to form a substituted or unsubstituted aryl ring or a heterocycle.

Examples of the substituent groups of the ring $A^{401}$ and the ring $A^{402}$ that form the ligands in the formula above are: halogen atoms such as chlorine, bromine, iodine and fluorine; substituted or unsubstituted alkyl groups such as a methyl group, an ethyl group, a propyl group, a butyl group, a sec-butyl group, a tert-butyl group, a pentyl group, a hexyl group, a heptyl group, an octyl group, a stearyl group and a trichloromethyl group; substituted or unsubstituted aryl groups such as a phenyl group, a naphthyl group a 3-methylphenyl group, a 3-methoxyphenyl group, a 3-fluorophenyl group, a 3-trichloromethylphenyl group, a 3-trifluoromethylphenyl group and a 3-nitrophenyl group; substituted or unsubstituted alkoxy groups such as a methoxy group, a n-butoxy group, a tert-butoxy group, a trichloromethoxy group, a trifluoroethoxy group, a pentafluoropropoxy group, a 2,2,3,3-tetrafluoropropoxy group, a 1,1,1,3,3,3-hexafluoro-2-propoxy group and a 6-(perfluorohethyl)hexyloxy group; substituted or unsubstituted aryloxy groups such as a phenoxy group, a p-nitrophenoxy group, a p-tert-butylphenoxy group, a 3-fluorophenoxy group, a pentafluorophenyl group and a 3-trifluoromethylphenoxy group; substituted or unsubstituted alkylthio groups such as a methylthio group, an ethylthio group, a tert-butylthio group, a hexylthio group, an octylthio group and a trifluoromethylthio group; substituted or unsubstituted arylthio groups such as a phenylthio group, a p-nitrophenylthio group, a p-tert-butylphenylthio group, a 3-fluorophenylthio group, a pentafluorophenylthio group and a 3-trifluoromethylphenylthio group; mono- or disubstituted amino groups such as a cyano group, a nitro group, an amino group, a methylamino group, a diethylamino group, an ethylamino group, a diethylamino group, a dipropylamino group, a dibutylamino group and a diphenylamino group; acylamino groups such as a bis(acetoxymethyl)amino group, a bis(acetoxyethyl)amino group, a bis(acetoxypropyl)amino group and a bis(acetoxybutyl)amino group; a hydroxyl group; a siloxy group; an acyl group; carbamoyl groups such as a methylcarbamoyl group, a dimethylcarbamoyl group, an ethylcarbamoyl group, a diethylcarbamoyl group, a propylcarbamoyl group, a butylcarbamoyl group, and a phenylcarbamoyl group; a carboxylic acid group; a sulfonic acid group; an imide group; cycloalkyl groups such as a cyclopentane group and a cyclohexyl group; aryl groups such as a phenyl group, a naphthyl group, a biphenyl group, an anthranil group, a phenanthryl group, a fluorenyl group and a pyrenyl group; and heterocyclic groups such as a pyridyl group, a pyrazinyl group, a pyrimidinyl group, a pyridazinyl group, a triazinyl group, an indolinyl group, a quinolyl group, an acridinyl group, a pyrrolidinyl group, a dioxanyl group, a piperidinyl group, a morpholidinyl group, a piperazinyl group, a carbazolyl group, a furanyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group and a benzoimidazolyl group. In addition, the substituent groups listed above may be bonded together to form a 6-membered aryl ring or a heterocycle.

As a preferred embodiment of the organic EL device according to the present invention, there is known a device containing a reductive dopant at a boundary between a region transporting the electrons or the cathode and an organic layer. The reductive dopant is defined as a substance capable of reducing an electron transporting compound. Thus, various substances having a certain level of reducibility can be used, preferable examples of which are at least one substance selected from a group consisting of: alkali metal, alkali earth metal, rare earth metal, an oxide of the alkali metal, a halogenide of the alkali metal, an oxide of the alkali earth metal, a halogenide of the alkali earth metal, an oxide of the rare earth metal, a halogenide of the rare earth metal, an organic complex of the alkali metal, an organic complex of the alkali earth metal and an organic complex of the rare earth metal.

Specifically, the reductive dopant is preferably a substance(s) having the work function of 2.9 eV or lower, which is exemplified by at least one alkali metal selected from a group consisting of Na (work function: 2.36 eV), K (work function: 2.28 eV), Rb (work function: 2.16 eV) and Cs (work function: 1.95 eV) or at least one alkali earth metal selected from a group consisting of Ca (work function: 2.9 eV), Sr (work function: 2.0 to 2.5 eV) and Ba (work function: 2.52 eV). Among these, the reductive dopant is more preferably at least one alkali metal selected from a group consisting of K, Rb and Cs, among which Rb and Cs are even more preferable and Cs is the most preferable. These alkali metals have particularly high reducibility, so that addition of a relatively small amount of these alkali metals to an electron injecting zone can enhance luminescence intensity and lifecycle of the organic electroluminescence device. In addition, as the reductive dopant having the work function of 2.9 eV or lower, a combination of two or more of these alkali metals is also preferable, and a combination including Cs is particularly preferable (e.g. combinations of Cs and Na, Cs and K, Cs and Rb or Cs, Na and K). The combinations including Cs can effectively exert the reducibility, so that the addition of such reductive dopant to the electron injecting zone can enhance the luminescence intensity and the lifecycle of the organic electroluminescence device.

According to the present invention, an electron injecting layer formed from an insulator or a semiconductor may be provided between the cathode and the organic layer. With the arrangement, leak of electric current can be effectively prevented and the electron injecting capability can be enhanced. As the insulator, it is preferable to use at least one metal compound selected from a group consisting of an alkali metal chalcogenide, an alkali earth metal chalcogenide, a halogenide of alkali metal and a halogenide of alkali earth metal. By forming the electron injecting layer from the alkali metal chalcogenide or the like, the electron injecting capability can preferably be further enhanced. Specifically, preferable examples of the alkali metal chalcogenide are $Li_2O$, LiO, $Na_2S$, $Na_2Se$ and NaO, while preferable example of the alkali earth metal chalcogenide are CaO, BaO, SrO, BeO, BaS and CaSe. Preferable examples of the halogenide of the alkali metal are LiF, NaF, KF, LiCl, KCl and NaCl. Preferable examples of the halogenide of the alkali earth metal are fluorides such as CaF2, $BaF_2$, $SrF_2$, $MgF_2$ and $BeF_2$, and halogenides other than the fluoride.

Examples of the semiconductor for forming the electron injecting layer are one of or a combination of two or more of an oxide, a nitride or an oxidized nitride containing at least one element selected from a group consisting of Ba, Ca, Sr, Yb, Al, Ga, In, Li, Na, Cd, Mg, Si, Ta, Sb and Zn. An inorganic compound for forming the electron injecting layer is preferably a microcrystalline or amorphous semiconductor film. When the electron injecting layer is formed of such semiconductor film, more uniform thin film can be formed, thereby reducing pixel defects such as a dark spot. Examples of such an inorganic compound are the above-described alkali metal chalcogenide, alkali earth metal chalcogenide, halogenide of the alkali metal and halogenide of the alkali earth metal.

[Cathode]

In order to inject the electrons into the electron injecting and transporting layers or the emitting layer, a material whose work function is small (4 eV or lower) is used as an electrode material for the cathode, examples of the material being metals, alloys, electrically conductive compounds and mixtures thereof. Examples of the electrode material are sodium, a sodium-potassium alloy, magnesium, lithium, a magnesium-silver alloy, aluminium/aluminium oxide, an aluminium-lithium alloy, indium, rare earth metal and the like.

The cathode is made by forming a thin film from the electrode material by vapor deposition and sputtering.

When the organic EL device is top-emission type, the cathode preferably transmits more than 10% of light emitted by the emitting layer.

The sheet resistance as the cathode is preferably several hundreds Ω/square or lower, and the thickness of the film is typically in a range from 10 nm to 1 μm, preferably 50 to 200 nm.

[Insulating Layer]

Since the electrical field is applied to ultra thin films in the organic electroluminescence device, pixel defects resulted from leak or short circuit are likely to occur. In order to prevent such defects, it is preferable to interpose an insulating thin film layer between a pair of electrodes.

Examples of a material used for the insulating layer are aluminum oxide, lithium fluoride, lithium oxide, cesium fluoride, cesium oxide, magnesium oxide, magnesium fluoride, calcium oxide, calcium fluoride, cesium fluoride, cesium carbonate, aluminium nitride, titanium oxide, silicon oxide, germanium oxide, silicon nitride, boron nitride, molybdenum oxide, ruthenium oxide, vanadium oxide and the like.

Mixtures or laminates thereof may also be used.

[Manufacturing Example(s) of Organic EL Device]

The organic EL device can be manufactured by forming the anode, the emitting layer and the cathode (in addition to the above, forming the hole injecting layer, the hole transporting layer, the electron injecting layer and the electron transporting layer as necessary) from the materials listed above by the above-described formation methods. The organic EL device can also be manufactured by forming the above elements in the inverse order of the above, namely from the cathode to the anode.

The following is a manufacturing example of the organic EL device in which the anode, the hole transporting layer, the emitting layer, the electron transporting layer and the cathode are sequentially formed on the light-transmissive substrate.

A thin film is formed of the anode material on a suitable light-transmissive substrate by vapor deposition or sputtering such that the thickness of the thin film is 1 μm or smaller, preferably in a range from 10 nm to 200 nm, thereby forming the anode. Then, the hole transporting layer is formed on the formed anode. The hole transporting layer may be formed by a method such as vacuum deposition, spin coating, casting and the LB method as described above, among which vacuum deposition is preferable in forming the hole transporting layer because the method can easily form homogeneous films and can prevent generation of pin holes. When the hole transporting layer is formed by vacuum deposition, conditions for conducting vacuum deposition depend on the compounds to be used (i.e., the material of the hole transporting layer), a crystal structure of the targeted hole transporting layer, and a recombination structure of the targeted hole transporting layer. Generally, conditions are preferably set so as to satisfy deposition-source temperature of 50 to 450 degrees C., vacuum of $10^{-7}$ to $10^{-3}$ torr, deposition speed of 0.01 to 50 nm/second, substrate temperature of −50 to 300 degrees C., film thickness of 5 nm to 5 μm.

Then, the emitting layer is formed on the hole transporting layer. The emitting layer may also be formed of a desirable material by a method such as vacuum deposition, sputtering, spin coating and casting, among which vacuum deposition is preferable in forming the emitting layer because the method can easily form homogeneous films and can prevent generation of pin holes. When the emitting layer is formed by vacuum deposition, deposition conditions for forming the emitting layer can be generally set in the same manner as the hole transporting layer although the deposition conditions may vary depending on compounds used for forming the emitting layer.

Next, the electron transporting layer is formed on the emitting layer. As with the hole transporting layer and the emitting layer, the electron transporting layer is also preferably formed by vacuum deposition so as to form a homogeneous film. Deposition conditions for forming the electron transporting layer can be set in the same manner as the hole transporting layer and the emitting layer.

Lastly, the cathode is laminated thereon.

The cathode can be formed from a metal by a method such as vapor deposition and sputtering. In order to protect the organic layers deposited under the cathode from being damaged, the vacuum deposition is preferable.

The above-described organic EL device is preferably manufactured such that all layers from the anode to the cathode are formed in one vacuuming.

The methods for forming each layer of the organic EL device are not particularly limited. Conventionally-known methods such as vacuum deposition, molecular-beam deposition, spin coating, dipping, casting, bar coating and roll coating are applicable to forming the layers.

Although the thickness of each organic layer of the organic EL device is not particularly limited, the thickness is generally preferably in a range of several nanometers to 1 μm because excessively-thinned film likely entails defects such as a pin hole while excessively-thickened film requires high voltage to be applied and deteriorates efficiency. When a voltage is applied to the organic EL device, the light-emission can be observed by applying a voltage of 3 to 40V with the anode having the positive polarity and the cathode having the negative polarity. When the voltage is applied with the inversed polarity, no current flows, so that no light is emitted. When an alternating voltage is applied, the uniform light-emission can be observed only when the anode has the positive polarity and the cathode has the negative polarity. A waveform of the alternating current to be applied may be suitably selected.

EXAMPLE

Next, the present invention will be further described in detail by exemplifying Examples. However, the present invention is not limited to such Examples.

Example 1

A 130 nm-thick transparent electrode formed of indium tin oxide was formed on a glass substrate having a size of 25 mm by 75 mm by 0.7 mm. After the transparent substrate was ultrasonically cleaned in isopropyl alcohol for five minutes, the substrate was further cleaned with UV (ultraviolet) ozone for thirty minutes, and then the substrate was mounted on a vapor deposition apparatus.

Initially, N,N'-bis[4-(N,N-diphenylamino)phenyl-1-yl]-N,N'-diphenyl-4,4'-benzidine was deposited on the substrate to form a 60 nm-thick hole injecting layer, and subsequently N,N'-bis[4'-{N-(naphthyl-1-yl)-N-phenyl}aminobiphenyl-4-yl]-N-phenylamine was deposited thereon to form a 10 nm-thick hole transporting layer. Then, the following compound (A-1), a naphthacene derivative, and the following compound (B-1), a compound having a pyrromethene skeleton, were simultaneously deposited thereon by weight ratio of 40 to 0.4 (=0.99 wt %) to form a 40 nm-thick emitting layer.

Compound (A-1)

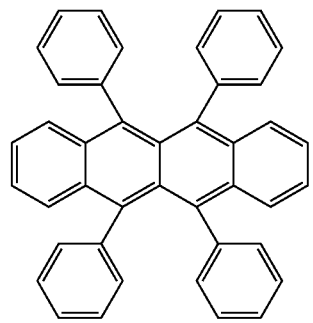

Compound (B-1)

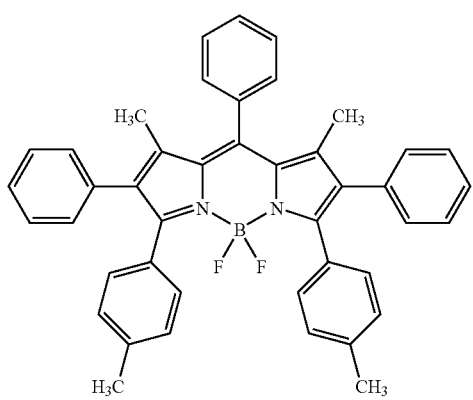

Next, the following compound (C-1) was deposited thereon to form a 30 nm-thick electron transporting layer.

Compound (C-1)

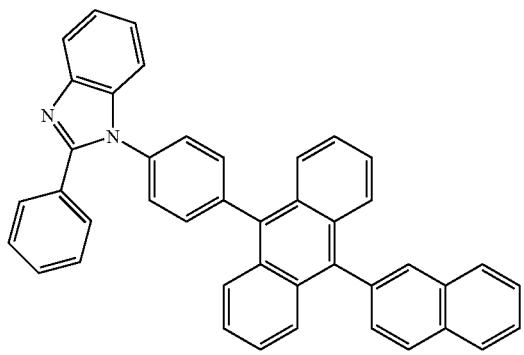

After 0.5 nm-thick lithium fluoride was subsequently deposited thereon, 150 nm-thick aluminum was deposited further thereon. The layer of aluminum/lithium fluoride served as the cathode. The organic EL device was manufactured by the above-described manner.

When a current test was conducted on the obtained device, the organic EL device was driven by a voltage of 4.7 V to emit red light having a luminescence intensity of 711 cd/m² at a current density of 10 mA/cm², a trichromatic coordinate of the emitted light was (0.66, 0.33), and efficiency of the device was 7.11 cd/A. In addition, when a continuous direct-current test was conducted with the initial luminescence intensity set at 5,000 cd/m², time elapsed until the luminescence intensity was reduced by half (i.e., time until half-life) was 1,800 hours.

Example 2

An organic EL device was manufactured in the same manner as in Example 1 except that the following compound (A-2) was used in place of the compound (A-1) for forming the emitting layer.

Compound (A-2)

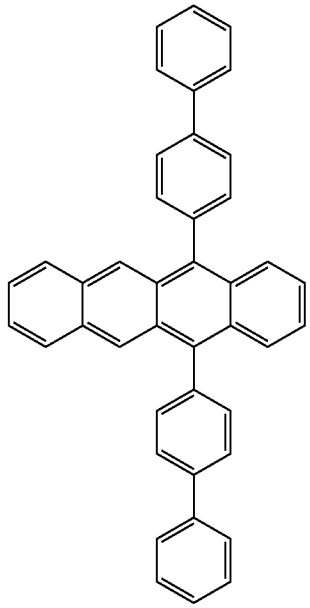

When a current test was conducted on the obtained device, the organic EL device was driven by a voltage of 4.8 V to emit red light having a luminescence intensity of 720 cd/m² at a current density of 10 mA/cm², a trichromatic coordinate of the emitted light was (0.66, 0.33), and efficiency of the device was 7.20 cd/A. In addition, when a continuous direct-current test was conducted with the initial luminescence intensity set at 5,000 cd/m², time elapsed until the luminescence intensity was reduced by half was 2,000 hours.

Example 3

An organic EL device was manufactured in the same manner as in Example 1 except that the following compound (A-3) was used in place of the compound (A-1) for forming the emitting layer.

Compound (A-3)

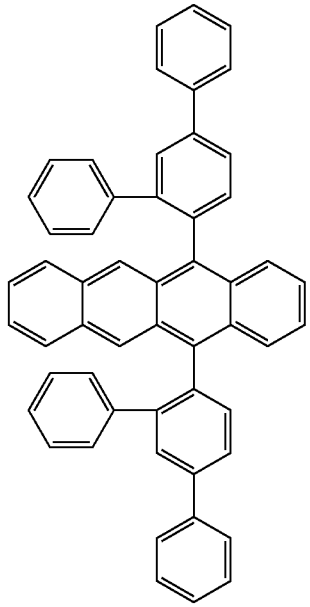

When a current test was conducted on the obtained device, the organic EL device was driven by a voltage of 4.8 V to emit red light having a luminescence intensity of 737 cd/m² at a current density of 10 mA/cm², a trichromatic coordinate of the emitted light was (0.66, 0.33), and efficiency of the device was 7.37 cd/A. In addition, when a continuous direct-current test was conducted with the initial luminescence intensity set at 5,000 cd/m², time elapsed until the luminescence intensity was reduced by half was 3,200 hours.

Example 4

An organic EL device was manufactured in the same manner as in Example 1 except that the following compound (B-2) was used in place of the compound (B-1) for forming the emitting layer.

Compound (B-2)

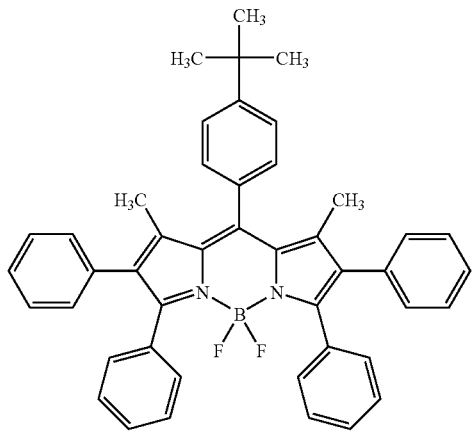

When a current test was conducted on the obtained device, the organic EL device was driven by a voltage of 4.8 V to emit red light having a luminescence intensity of 698 cd/m² at a current density of 10 mA/cm², a trichromatic coordinate of the emitted light was (0.66, 0.33), and efficiency of the device was 6.98 cd/A. In addition, when a continuous direct-current test was conducted with the initial luminescence intensity set at 5,000 cd/m², time elapsed until the luminescence intensity was reduced by half was 1,900 hours.

Example 5

An organic EL device was manufactured in the same manner as in Example 1 except that the following compound (B-3) was used in place of the compound (B-1) for forming the emitting layer.

Compound (B-3)

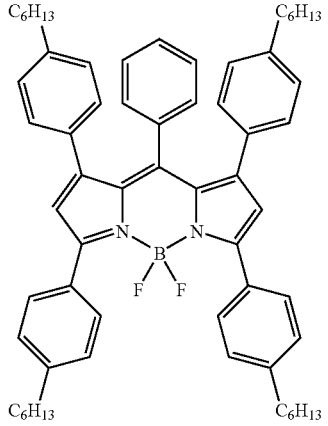

When a current test was conducted on the obtained device, the organic EL device was driven by a voltage of 4.8 V to emit red light having a luminescence intensity of 710 cd/m² at a current density of 10 mA/cm², a trichromatic coordinate of the emitted light was (0.66, 0.33), and efficiency of the device was 7.10 cd/A. In addition, when a continuous direct-current test was conducted with the initial luminescence intensity set at 5,000 cd/m², time elapsed until the luminescence intensity was reduced by half was 1,500 hours.

Example 6

An organic EL device was manufactured in the same manner as in Example 1 except that the following compound (B-4) was used in place of the compound (B-1) for forming the emitting layer.

Compound (B-4)

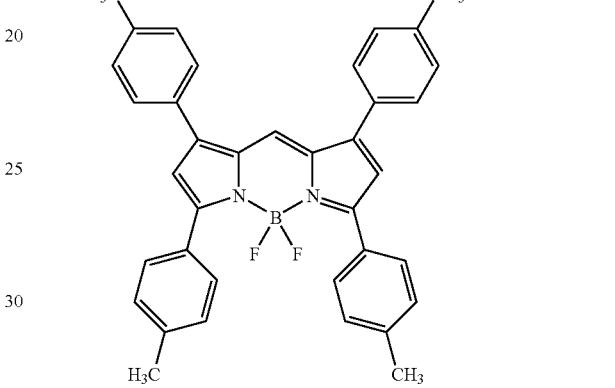

When a current test was conducted on the obtained device, the organic EL device was driven by a voltage of 4.7 V to emit red light having a luminescence intensity of 676 cd/m² at a current density of 10 mA/cm², a trichromatic coordinate of the emitted light was (0.66, 0.33), and efficiency of the device was 6.76 cd/A. In addition, when a continuous direct-current test was conducted with the initial luminescence intensity set at 5,000 cd/m², time elapsed until the luminescence intensity was reduced by half was 1,600 hours.

Example 7

An organic EL device was manufactured in the same manner as in Example 1 except that the following compound (C-2) was used in place of the compound (C-1) for forming the electron transporting layer.

Compound (C-2)

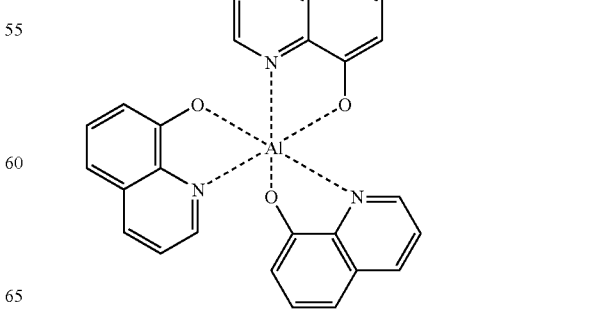

When a current test was conducted on the obtained device, the organic EL device was driven by a voltage of 5.6 V to emit red light having a luminescence intensity of 564 cd/m$^2$ at a current density of 10 mA/cm$^2$, a trichromatic coordinate of the emitted light was (0.64, 0.34), and efficiency of the device was 5.64 cd/A. In addition, when a continuous direct-current test was conducted with the initial luminescence intensity set at 5,000 cd/m$^2$, time elapsed until the luminescence intensity was reduced by half was 1,000 hours.

[Comparative 1]

An organic EL device was manufactured in the same manner as in Example 7 except that the following compound (C-2) was used in place of the compound (A-1) for forming the emitting layer.

When a current test was conducted on the obtained device, the organic EL device was driven by a voltage of 6.1 V to emit red light having a luminescence intensity of 434 cd/m$^2$ at a current density of 10 mA/cm$^2$, a trichromatic coordinate of the emitted light was (0.63, 0.35), and efficiency of the device was 4.34 cd/A. In addition, when a continuous direct-current test was conducted with the initial luminescence intensity set at 5,000 cd/m$^2$, time elapsed until the luminescence intensity was reduced by half was 500 hours.

[Comparative 2]

An organic EL device was manufactured in the same manner as in Example 1 except that the following compound (B-5) was used in place of the compound (B-1) for forming the emitting layer.

Compound (B-5)

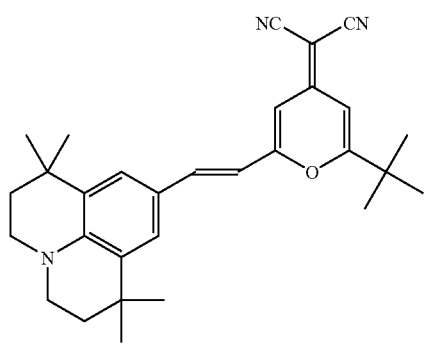

When a current test was conducted on the obtained device, the organic EL device was driven by a voltage of 4.7 V to emit red light having a luminescence intensity of 385 cd/m$^2$ at a current density of 10 mA/cm$^2$, a trichromatic coordinate of the emitted light was (0.64, 0.37), and efficiency of the device was 3.85 cd/A. In addition, when a continuous direct-current test was conducted with the initial luminescence intensity set at 5,000 cd/m$^2$, time elapsed until the luminescence intensity was reduced by half was 700 hours.

[Comparative 3]

An organic EL device was manufactured in the same manner as in Example 1 except that the following compound (C-2) was used in place of the compound (A-1) for forming the emitting layer.

When a current test was conducted on the obtained device, the organic EL device was driven by a voltage of 5.2 V to emit red light having a luminescence intensity of 451 cd/m$^2$ at a current density of 10 mA/cm$^2$, a trichromatic coordinate of the emitted light was (0.65, 0.33), and efficiency of the device was 4.51 cd/A. In addition, when a continuous direct-current test was conducted with the initial luminescence intensity set at 5,000 cd/m$^2$, time elapsed until the luminescence intensity was reduced by half was 600 hours.

Example 8

An organic EL device was manufactured in the same manner as in Example 1 except that the following compound (B-6) was used in place of the compound (B-1) for forming the emitting layer.

Compound (B-6)

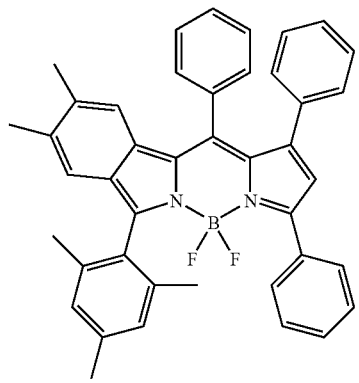

When a current test was conducted on the obtained device, the organic EL device was driven by a voltage of 4.4 V to emit red light having a luminescence intensity of 1,081 cd/m$^2$ at a current density of 10 mA/cm$^2$, a trichromatic coordinate of the emitted light was (0.65, 0.34), and efficiency of the device was 10.81 cd/A. In addition, when a continuous direct-current test was conducted with the initial luminescence intensity set at 5,000 cd/m$^2$, time elapsed until the luminescence intensity was reduced by half was 3,500 hours.

Example 9

An organic EL device was manufactured in the same manner as in Example 1 except that the following compound (B-7) was used in place of the compound (B-1) for forming the emitting layer.

Compound (B-7)

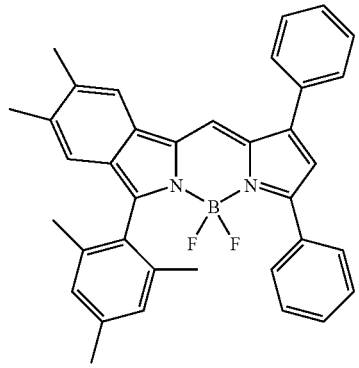

When a current test was conducted on the obtained device, the organic EL device was driven by a voltage of 4.5 V to emit red light having a luminescence intensity of 852 cd/m$^2$ at a current density of 10 mA/cm$^2$, a trichromatic coordinate of the emitted light was (0.67, 0.33), and efficiency of the device was 8.52 cd/A. In addition, when a continuous direct-current test was conducted with the initial luminescence intensity set at 5,000 cd/m$^2$, time elapsed until the luminescence intensity was reduced by half was 3,300 hours.

TABLE 1

|  | Drive Voltage (V) | luminescence intensity (cd/m²) | trichromatic coordinate | Luminous Efficiency (cd/A) | time until half-life (hr) |
|---|---|---|---|---|---|
| Example 1 | 4.7 | 711 | (0.66, 0.33) | 7.11 | 1,800 |
| Example 2 | 4.8 | 720 | (0.66, 0.33) | 7.20 | 2,000 |
| Example 3 | 4.8 | 737 | (0.66, 0.33) | 7.37 | 3,200 |
| Example 4 | 4.8 | 698 | (0.66, 0.33) | 6.98 | 1,900 |
| Example 5 | 4.8 | 710 | (0.66, 0.33) | 7.10 | 1,500 |
| Example 6 | 4.7 | 676 | (0.66, 0.33) | 6.76 | 1,600 |
| Example 7 | 5.6 | 564 | (0.64, 0.34) | 5.64 | 1,000 |
| Comparative 1 | 6.1 | 434 | (0.63, 0.35) | 4.34 | 500 |
| Comparative 2 | 4.7 | 385 | (0.64, 0.37) | 3.85 | 700 |
| Comparative 3 | 5.2 | 451 | (0.65, 0.33) | 4.51 | 600 |
| Example 8 | 4.4 | 1,081 | (0.65, 0.34) | 10.81 | 3,500 |
| Example 9 | 4.5 | 852 | (0.67, 0.33) | 8.52 | 3,300 |

It is understood from a comparison between Example 7 and Comparative 1 that Example 7, in which the compound (A-1) was used as the host, is more excellent in drive voltage, luminescence intensity, chromaticity and time until half-life.

In other words, a combination of the compound (A-1) and the compound (B-1) as the combination of the host and the dopant is more excellent than a combination of the compound (C-2), a general host material, and the compound (B-1).

In Examples 1 to 6 and Comparatives 2 and 3, the compound (C-1) was used as the electron transporting layer. The compound (B-5) was used as the dopant in Comparative 2 while the compound (C-2) was used as the host in Comparative 3. In contrast, the combination of the host and the dopant according to the present invention was used in Examples 1 to 6.

Consequently, the combination of the host and the dopant according to the present invention is excellent in terms of drive voltage, luminescence intensity, chromaticity, luminous efficiency and time until half-life.

In other words, irrespective of what compound is used for forming the electron transporting layer, the combination of the host material and the dopant material according to the present invention is excellent in terms of drive voltage, luminescence intensity, chromaticity, efficiency and time until half-life.

It is understood from a comparison between Examples 1 to 6 and Example 7 that, by using such a material as represented by the compound (C-1) according to the present invention for the electron transporting material, the device can exhibit excellent performance in terms of drive voltage, luminescence intensity, chromaticity, efficiency, time until half-time and the like.

The emitting region is typically preferably located within the emitting layer in the organic EL device.

On the other hand, an emitting material for emitting red light tends to cause electron traps because an energy gap of the dopant is small. Accordingly, the electrons injected into the emitting layer from the electron transporting layer tend to be trapped in the dopant located adjacent to the electron transporting layer, thereby moving the emitting region toward the electron transporting layer.

In Example 7, the chromaticity was shifted toward green, and the compound (C-2) emitted light. It can be deduced from the above with respect to Example 7 that the holes were more strongly injected into the emitting layer than the electrons, and that many of the holes penetrated the emitting layer to reach the electron transporting layer, thereby generating exciters in the compound (C-2) forming the electron transporting layer. In addition, since the compound (C-2) emitted light, the time elapsed until the lifetime of the organic EL device was reduced by half is short.

In this respect, the electron transporting material according to the present invention, a representative example of which is the compound (C-1), is excellent in transporting electrons. The electron transporting layer formed of such an electron transporting material can strongly inject the electrons into the emitting layer, thereby preventing the holes from penetrating the emitting layer to reach the electron transporting layer.

In other words, the organic EL device according to the present invention can emit light of high chromaticity with high efficiency while preventing generation of exciters in the electron transporting layer, and lifetime of the entire device is long.

In addition, when a naphthacene derivative and a compound having pyrromethene skeleton or the like are respectively used for the host and the dopant, the electron transporting material can exhibit above-described excellent effects and advantages.

Lifetime of Example 3 is much longer than those of Examples 1 and 2 because the compound A-3 was used for the host in Example 3. It has been revealed from the above that substituent(s) in ortho position(s) of benzene rings bonded to the naphthacene skeleton prevents molecular association, thereby contributing to longer lifetime.

The present invention is not limited to the above examples, but includes modifications and improvements made within a scope where an object of the present invention can be achieved.

For instance, ruburene, which is an example of the host material of Example 1, may be substituted or unsubstituted. In addition, the compounds used in the other Examples may be substituted or unsubstituted.

The priority application Number JP2007-061091 upon which this patent application is based is hereby incorporated by reference.

What is claimed is:

1. An organic electroluminescence device, comprising:
   a cathode;
   an anode; and
   an emitting layer provided between the cathode and the anode, wherein
   the emitting layer comprises a host and a dopant,
   the host is a naphthacene derivative represented by formula (3) as follows, and
   the dopant is a compound having a pyrromethene skeleton represented by formula (2) as follows or a metal complex of the compound of formula (2),

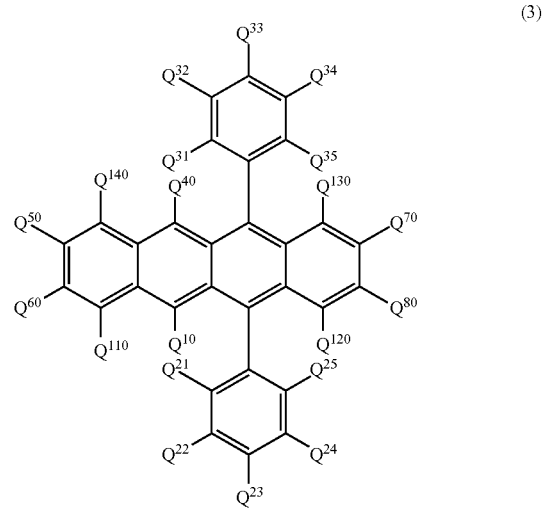

(3)

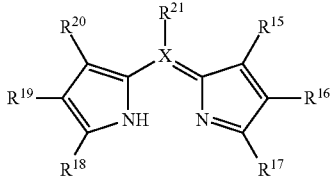

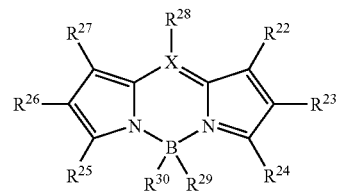

wherein $Q^{10}$, $Q^{21}$ to $Q^{25}$, $Q^{31}$ to $Q^{35}$, $Q^{40}$ to $Q^{80}$ and $Q^{110}$ to $Q^{140}$ each represent a hydrogen atom, a substituted or unsubstituted alkyl group, a substituted or unsubstituted aryl group, a substituted or unsubstituted amino group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, or a substituted or unsubstituted heterocyclic group, $Q^{10}$, $Q^{21}$ to $Q^{25}$, $Q^{31}$ to $Q^{35}$, $Q^{40}$ to $Q^{80}$ and $Q^{110}$ to $Q^{140}$ being allowed to be mutually the same or different, adjacent two or more of $Q^{21}$ to $Q^{25}$ and $Q^{31}$ to $Q^{35}$ being allowed to be mutually bonded to form a cyclic structure, at least two of $Q^{21}$ to $Q^{25}$ and at least two of $Q^{31}$ to $Q^{35}$ represent a substituted or unsubstituted alkyl group, a substituted or unsubstituted aryl group, a substituted or unsubstituted amino group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, or a substituted or unsubstituted heterocyclic group, and at least one of $R^{15}$ to $R^{21}$ is a substituent having an aromatic ring or forming a condensed ring together with an adjacent substituent while the rest of $R^{15}$ to $R^{21}$ each represents a hydrogen atom, an alkyl group, a cycloalkyl group, an aralkyl group, an alkenyl group, a cycloalkenyl group, an alkynyl group, a hydroxyl group, a mercapto group, an alkoxy group, an alkylthio group, an arylether group, an arylthioether group, an aryl group, a heterocyclic group, halogen, a haloalkane, a haloalkene, a haloalkyne, a cyano group, an aldehyde group, a carbonyl group, a carboxyl group, an ester group, a carbamoyl group, an amino group, a nitro group, a silyl group or a siloxanyl group, the rest of $R^{15}$ to $R^{21}$ may optionally form a condensed ring or an aliphatic ring with an adjacent substituent, the groups listed above each having 1 to 20 carbon atoms, $R^{15}$ to $R^{21}$ being allowed to be mutually the sane or different and being allowed to be substituted or unsubstituted; X representing a carbon atom or a nitrogen atom on a condition that $R^{21}$ above does not exist when X represents a nitrogen atom; and a metal in the metal complex being at least one metal selected from a group consisting of boron, beryllium, magnesium, chrome, iron, cobalt, nickel, copper, zinc and platinum.

2. The organic electroluminescence device according to claim 1, wherein the compound having the pyrromethene skeleton represented by the formula (2) or the metal complex of the compound is a metal complex having a pyrromethene skeleton represented by a formula (2-1) as follows, where: at least one of $R^{22}$ to $R^{28}$ is a substitute having an aromatic ring or forms a condensed aromatic ring together with an adjacent substituent while the rest of $R^{22}$ to $R^{28}$ each represent a hydrogen atom, an alkyl group, a cycloalkyl group, an aralkyl group, an alkenyl group, a cycloalkenyl group, an alkynyl group, a hydroxyl group, a mercapto group, an alkoxy group, an alkylthio group, an arylether group, an arylthioether group, an aryl group, a heterocyclic group, halogen, haloalkane, haloalkene, haloalkyne, a cyano group, an aldehyde group, a carbonyl group, a carboxyl group, an ester group, a carbamoyl group, an amino group, a nitro group, a silyl group or a siloxanyl group, the rest of $R^{22}$ to $R^{28}$ each being allowed to form a condensed ring or an aliphatic ring with an adjacent substituent, $R^{22}$ to $R^{28}$ being allowed to be mutually the same or different and being allowed to be substituted or unsubstituted; $R^{29}$ and $R^{30}$ are allowed to be mutually the same or different and each are selected from a group consisting of halogen, a hydrogen atom, substituted or unsubstituted alkyl, substituted or unsubstituted aryl and a substituted or unsubstituted heterocyclic group; and X represents a carbon atom or a nitrogen atom on a condition that $R^{28}$ above does not exist when X represents a nitrogen atom.

3. The organic electroluminescence device according to claim 2, wherein at least one of $R^{22}$ to $R^{28}$ in the metal complex having the pyrromethene skeleton represented by the formula (2-1) is a substituent having an aromatic ring.

4. The organic electroluminescence device according to claim 2, wherein at least one of $R^{22}$ to $R^{28}$ in the metal complex having the pyrromethene skeleton represented by the formula (2-1) forms a condensed aromatic ring together with an adjacent substituent.

5. The organic electroluminescence device according to claim 4, wherein at least one of $R^{22}$ to $R^{24}$ in the metal complex having the pyrromethene skeleton represented by the formula (2-1) forms a substituted or unsubstituted condensed aromatic ring together with an adjacent substituent and/or at least one of $R^{25}$ to $R^{27}$ in the metal complex having the pyrromethene skeleton represented by the formula (2-1) forms a substituted or unsubstituted condensed aromatic ring together with an adjacent substituent.

6. The organic electroluminescence device according to claim 2, wherein the metal complex having the pyrromethene skeleton represented by the formula (2-1) is a metal complex having a pyrromethene skeleton represented by a formula (2-2) as follows,

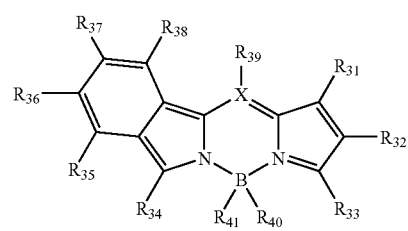

where: $R_{31}$ to $R_{39}$ each represent a hydrogen atom, an alkyl group, a cycloalkyl group, an aralkyl group, an alkenyl group, a cycloalkenyl group, an alkynyl group, a hydroxyl group, a mercapto group, an alkoxy group, an alkylthio group, an arylether group, an arylthioether group, an aryl group, a heterocyclic group, halogen, haloalkane, haloalkene, haloalkyne, a cyano group, an aldehyde group, a carbonyl group, a carboxyl group, an ester group, a carbamoyl group, an amino group, a nitro group, a silyl group or a siloxanyl group, $R_{31}$ to $R_{39}$ being allowed to be mutually the same or different and being allowed to be substituted or unsubstituted; $R_{40}$ and $R_{41}$ are allowed to be mutually the same or different and each are selected from a group consisting of halogen, a hydrogen atom, substituted or unsubstituted alkyl, substituted or unsubstituted aryl and a substituted or unsubstituted heterocyclic group; and X represents a carbon atom or a nitrogen atom on a condition that $R_{39}$ above does not exist when X represents a nitrogen atom.

7. The organic electroluminescence device according to claim 4, wherein the metal complex having the pyrromethene skeleton represented by the formula (2-1) is a metal complex having a pyrromethene skeleton represented by a formula (2-3) as follows,

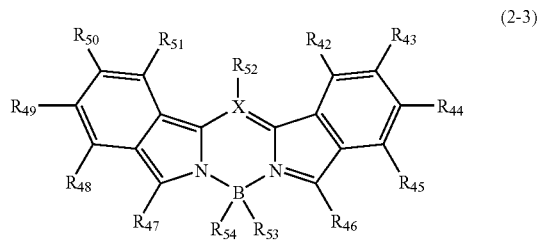

(2-3)

where: $R_{42}$ to $R_{52}$ each represent a hydrogen atom, an alkyl group, a cycloalkyl group, an aralkyl group, an alkenyl group, a cycloalkenyl group, an alkynyl group, a hydroxyl group, a mercapto group, an alkoxy group, an alkylthio group, an arylether group, an arylthioether group, an aryl group, a heterocyclic group, halogen, haloalkane, haloalkene, haloalkyne, a cyano group, an aldehyde group, a carbonyl group, a carboxyl group, an ester group, a carbamoyl group, an amino group, a nitro group, a silyl group or a siloxanyl group, $R_{42}$ to $R_{52}$ being allowed to be mutually the same or different and being allowed to be substituted or unsubstituted; $R_{53}$ and $R_{54}$ are allowed to be mutually the same or different and each are selected from a group consisting of halogen, a hydrogen atom, a substituted or unsubstituted alkyl, a substituted or unsubstituted aryl and a substituted or unsubstituted heterocyclic group; and X represents a carbon atom or a nitrogen atom on a condition that $R_{52}$ above does not exist when X represents a nitrogen atom.

8. The organic electroluminescence device according to claim 1, wherein at least one of $Q^{21}$, $Q^{25}$, $Q^{31}$ and $Q^{35}$ represents a substituted or unsubstituted alkyl group, a substituted or unsubstituted aryl group, a substituted or unsubstituted amino group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, or a substituted or unsubstituted heterocyclic group.

9. The organic electroluminescence device according to claim 1, wherein at least one of $Q^{21}$ and $Q^{25}$ represents a substituted or unsubstituted aryl group or a substituted or unsubstituted heterocyclic group while at least one of $Q^{31}$ and $Q^{35}$ represents a substituted or unsubstituted aryl group or a substituted or unsubstituted heterocyclic group.

10. The organic electroluminescence device according to claim 1, wherein the dopant is contained in the emitting layer at a doping concentration of 0.1 to 10 mass %.

11. The organic electroluminescence device according to claim 10, wherein the dopant is contained in the emitting layer at a doping concentration of 0.5 to 2.0 mass %.

12. The organic electroluminescence device according to claim 1, further comprising an electron transporting layer provided between the cathode and the anode, wherein the electron transporting layer comprises a compound represented by a formula (4) as follows, $$(A)_m\text{-}(B)_n \quad (4)$$

where: A represents a substituted or unsubstituted condensed aromatic hydrocarbon group having three or more rings; B represents a substituted or unsubstituted heterocyclic group; and m and n each represent an integer in a range of 1 to 6.

13. The organic electroluminescence device according to claim 12, wherein A in the compound represented by the formula (4) has a skeleton in its molecule, the skeleton selected from a group consisting of anthracene, phenanthrene, naphthacene, pyrene, chrysene, benzoanthracene, pentacene, dibenzoanthracene, benzopyrene, fluorene, benzofluorene, fluoranthene, benzofluoranthene, naphthofluoranthene, dibenzofluorene, dibenzopyrene and dibenzofluoranthene.

14. The organic electroluminescence device according to claim 12, wherein B in the compound represented by the formula (4) is a nitrogen-containing heterocyclic group.

15. The organic electroluminescence device according to claim 14, wherein B in the compound represented by the formula (4) has a skeleton in its molecule, the skeleton selected from a group consisting of pyridine, pyrimidine, pyrazine, pyridazine, triazine, quinoline, quinoxaline, acridine, imidazopyridine, imidazopyrimidine, phenanthroline, pyrazole, imidazole and benzoimidazole.

16. The organic electroluminescence device according to claim 15, wherein
the compound represented by the formula (4) is a benzoimidazole derivative represented by a formula (5) or a formula (6) as follows,

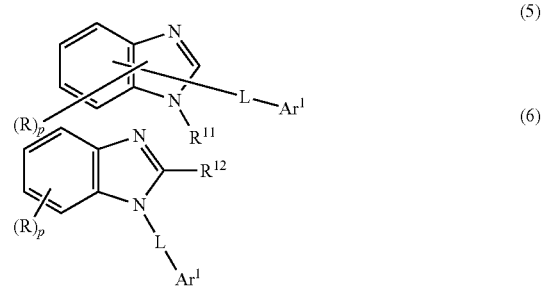

where: R represents a hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms or a substituted or unsubstituted alkoxy group having 1 to 20 carbon atoms; p represents an integer in a range of 1 to 4; $R^{11}$ represents a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms or an alkoxy group having 1 to 20 carbon atoms; $R^{12}$ represents a hydrogen atom, a substituted or unsubstituted aryl group having 6 to 60 carbon atoms, a substituted or unsubstituted pyridyl group, a substituted or unsubstituted quinolyl group, a substituted or unsubstituted alkyl group having 1 to 20 carbon atoms or a substituted or unsubstituted alkoxy group having 1 to 20 carbon atoms; L represents a substituted or unsubstituted arylene group having 6 to 60 carbon atoms, a substituted or unsubstituted pyridinylene group, a substituted or unsubstituted quinolinylene group or a substituted or unsubstituted fluorenylene group; and $Ar^1$ represents a substituted or unsubstituted aryl group having 6 to 60 carbon atoms, a substituted or unsubstituted pyridyl group or a substituted or unsubstituted quinolyl group, at least one of R, $R^{11}$, $R^{12}$, L and $Ar^1$ corresponding to A in the compound represented by the formula (4) and being a condensed aromatic hydrocarbon group having three or more rings.

17. The organic electroluminescence device according to claim 1, wherein the emitting layer emits light of orange to red.

18. A display, comprising the organic electroluminescence device according to claim 1.

\* \* \* \* \*